United States Patent
Ikuta et al.

(10) Patent No.: US 10,732,400 B2
(45) Date of Patent: Aug. 4, 2020

(54) SPECTRALLY ENCODED PROBE WITH MULTIPLE DIFFRACTION ORDERS

(71) Applicants: Canon U.S.A., Inc., Melville, NY (US); The General Hospital Corporation, Boston, MA (US)

(72) Inventors: Mitsuhiro Ikuta, Cambridge, MA (US); Dongkyun Kang, Tucson, AZ (US); Dukho Do, Anyang-si (KR); Guillermo Tearney, Cambridge, MA (US)

(73) Assignees: Canon U.S.A., Inc., Melville, NY (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 16/509,292

(22) Filed: Jul. 11, 2019

(65) Prior Publication Data
US 2019/0339507 A1 Nov. 7, 2019

Related U.S. Application Data

(63) Continuation of application No. 15/418,329, filed on Jan. 27, 2017, now Pat. No. 10,401,610.

(60) Provisional application No. 62/363,119, filed on Jul. 15, 2016.

(51) Int. Cl.
| | | |
|---|---|---|
| *G02B 23/24* | (2006.01) | |
| *A61B 1/00* | (2006.01) | |
| *A61B 1/06* | (2006.01) | |
| *A61B 1/07* | (2006.01) | |

(Continued)

(52) U.S. Cl.
CPC ...... *G02B 23/2407* (2013.01); *A61B 1/00096* (2013.01); *A61B 1/00172* (2013.01); *A61B 1/0638* (2013.01); *A61B 1/07* (2013.01); *G02B 23/2423* (2013.01); *G02B 23/2469* (2013.01); *G02B 27/4227* (2013.01);

(Continued)

(58) Field of Classification Search
CPC .................. G02B 23/2407; A61B 1/00096
See application file for complete search history.

(56) References Cited

U.S. PATENT DOCUMENTS

| | | | | |
|---|---|---|---|---|
| 2003/0223248 A1* | 12/2003 | Cronin | ...................... | G01J 3/10 362/555 |
| 2011/0237892 A1* | 9/2011 | Tearney | ............... | A61B 5/0062 600/160 |
| 2012/0176615 A1* | 7/2012 | Brown | ............... | G01B 9/02004 356/328 |

FOREIGN PATENT DOCUMENTS

| | | |
|---|---|---|
| CN | 101360447 A | 2/2009 |
| CN | 101797146 A | 8/2010 |
| CN | 102665622 A | 9/2012 |

(Continued)

OTHER PUBLICATIONS

Kang etal Miniature Grating for Spectrally-Encoded Endoscopy, May 7, 2013;Lab Chip. 13(9): 1810-1816. doi: 10.1039/c3lc50076d. (Year: 2013).*

*Primary Examiner* — Girumsew Wendmagegn
(74) *Attorney, Agent, or Firm* — Canon U.S.A., Inc. I.P. Division

(57) ABSTRACT

A spectrally encoded endoscopic probe. The probe has a light guiding component, a light focusing component, and a grating component. The probe is configured such that a set of light beams of multiple wavelengths are diffracted by the grating component in different orders at substantially the same angle. The set of light beams includes at least 3 light beams. Each light beam among the set of light beams is associated with a different wavelength.

22 Claims, 12 Drawing Sheets

(51) Int. Cl.
*G02B 27/42* (2006.01)
*H04N 5/225* (2006.01)

(52) U.S. Cl.
CPC ........ *H04N 5/2256* (2013.01); *A61B 1/00009* (2013.01); *H04N 2005/2255* (2013.01)

(56) References Cited

FOREIGN PATENT DOCUMENTS

| | | |
|---|---|---|
| JP | 2011-527930 A | 11/2011 |
| JP | 2017-505667 A | 2/2017 |
| JP | 2017-506531 A | 3/2017 |

\* cited by examiner

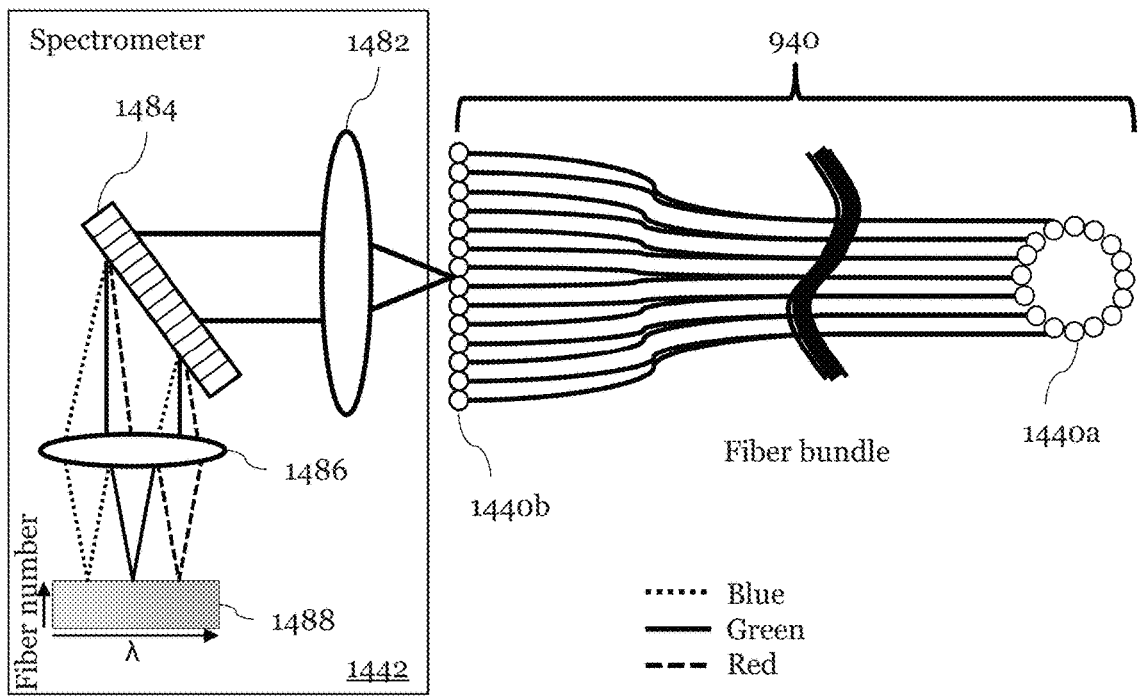
FIG. 14
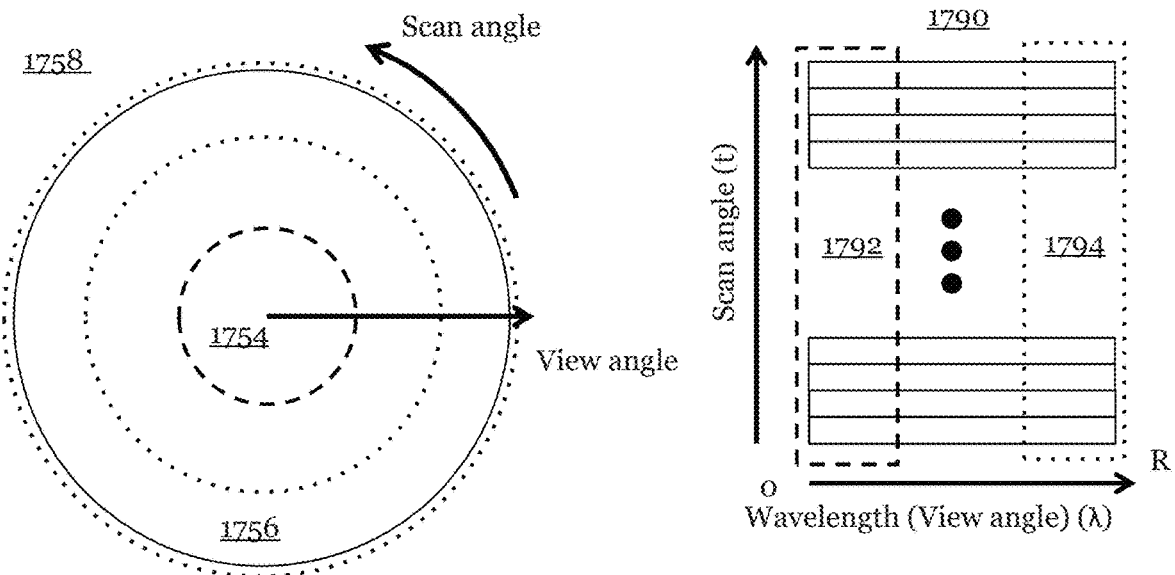
FIG. 17A
FIG. 17B ns SPECTRALLY ENCODED PROBE WITH
MULTIPLE DIFFRACTION ORDERS

CROSS-REFERENCE TO RELATED
APPLICATIONS

This application is a continuation, and claims the benefit, of U.S. patent application Ser. No. 15/418,329, presently pending and filed on Jan. 27, 2017, which claims the benefit of U.S. Provisional Pat. Application No. 62/363,119, filed Jul. 15, 2016, all of which applications are hereby incorporated by reference herein in their entireties.

BACKGROUND

Field of Art

The present disclosure relates to endoscopes. More particularly, the disclosure exemplifies spectrally encoded endoscopic probes.

Description of the Related Art

Medical probes have the ability to provide images from inside the patient's body. Considering the potential damage to a human body caused by the insertion of a foreign object, it is preferable for the probe to be as small as possible. Additionally, the ability to image within small pathways such as small vessels, small ducts, small needles, cracks etc., requires a small probe size.

One useful medical probe employs spectrally encoded endoscopy ("SEE") technology, which is a miniature endoscopy technology that can conduct high-definition imaging through a sub-mm diameter probe. SEE uses wavelength to encode spatial information of a sample, thereby allowing high-resolution imaging to be conducted through small diameter endoscopic probes. SEE can be accomplished using broad bandwidth light input into one or more optical fibers. At the distal end of the fiber, a diffractive or dispersive optical component disperses the light across the sample, which returns back through the optic and then through optical fibers. Light is detected by a wavelength detecting apparatus, such as a spectrometer where each resolvable wavelength corresponds to reflectance from a different point on the sample. The principle of the SEE technique and an SEE probe with a diameter of 0.5 mm, i.e., 500 μm have been described, for example, in D. Yelin et al., Nature Vol. 443, 765-765 (2006) as well as in U.S. Patent Publication Nos. 2007/0233396 and 2008/0013960. SEE can produce high-quality images in two-dimensions and three-dimensions.

By detecting the light intensity as a function of wavelength, the image may be reconstructed. However, since SEE images utilize wavelength information to encode spatial location therefore important color information is lost or convoluted with the spatial information. Conventional endoscopy can use color information as a cue for diagnosis.

Previously, methods for conducting color imaging in an SEE probe have been proposed. The use of three excitation fibers for color SEE imaging in a bench top setup was demonstrated (Optics Express, 17 (17), 15239-15247; 2009 and U.S. Pat. No. 9,254,089). In this bench top setup, three light beams, each with one of the red, green, and blue spectral bands, were used. These light beams were incident on the grating at different angles, which resulted in same diffraction angle for all three spectral bands. Therefore, each point on the tissue was illuminated with three spectral bands.

However, this system is not easily manufactured and assembled and multiple fibers must be sent through a multiple channel rotary junction for use in in vivo imaging. The multiple fibers increase the size of the probe which reduces the number of applicable uses and invasiveness of use. Additionally, other solutions for color SEE which included multiple grating patterns on a small grating surface can be difficult and/or expensive to fabricate and combine into the SEE apparatus. What is needed is a probe that overcomes these deficiencies of past systems.

SUMMARY

Accordingly, it can be beneficial to address and/or overcome at least some of the deficiencies indicated herein above, and thus to provide a new color SEE probe that can provide color viewing without the size, rotary junction, or fabrication demands of prior systems.

At least a first embodiment, may be a spectrally encoded endoscopy probe for color imaging. The probe may comprise: a light guiding component for guiding illumination light; a light focusing component; and a grating component. The spectrally encoded endoscopy probe is configured such that a set of light beams of multiple wavelengths may be diffracted by the grating component in different orders at a same angle. The set of light beams includes at least 3 light beams. Each light beam among the set of light beams may be associated with a different wavelength.

In an aspect of the first embodiment, the multiple wavelengths may be between 400 nm and 1200 nm. The minimum value for an absolute value of the different orders may be 2.

In an aspect of the first embodiment, the multiple wavelengths may be between 400 nm and 800 nm. The minimum value for an absolute value of the different orders may be 3.

In an aspect of the first embodiment, each light beam among the set of light beams may be associated with a different wavelength range among a plurality of wavelength ranges. Each light beam may be diffracted in a different diffraction order. Each light beam may be diffracted at substantially the same angle range.

In an aspect of the first embodiment, the spectral width of each wavelength range among the plurality of wavelength ranges may be more than 30 nm.

In an aspect of the first embodiment, the angle range may be more than 10 degrees.

In an aspect of the first embodiment the light guiding component may consist of a single optical fiber.

In an aspect of the first embodiment the illumination light may comprise broadband visible light.

In an aspect of the first embodiment the spectrally dispersed light exiting the grating component may have a wavelength of between 400 nm and 1000 nm, and may not be diffracted in zeroth order of transmission.

In an aspect of the first embodiment the multiple orders of spectrally dispersed light may be the $-m^{th}$, $-(m+1)^{th}$, and $-(m+2)^{th}$ orders, and wherein m is an integer.

In an aspect of the first embodiment the multiple orders of spectrally dispersed light may be a set of orders selected from: a first set consisting of a $-3^{rd}$ order, a $-4^{th}$ order and a $-5^{th}$ order; a second set consisting of the $-4^{th}$ order, the $-5^{th}$ order, and a $-6^{th}$ order; and a third set consisting of the $-5^{th}$ order, the $-6^{th}$ order, and a $-7^{th}$ order.

In an aspect of the first embodiment, the spectrally dispersed light exiting the grating component may not be diffracted in zeroth order of transmission.

In an aspect of the first embodiment, the light focusing component may be a gradient index (GRIN) lens or a ball lens.

In an aspect of the first embodiment the probe may be a forward view probe.

In an aspect of the first embodiment the probe may be a side view probe.

In an aspect of the first embodiment an absolute value of product of a spatial frequency of the grating component and one of the orders of the multiple orders may be greater than 2000/mm.

In an aspect of the first embodiment the grating component may be a binary grating having a groove depth of greater than 1.0 µm.

In an aspect of the first embodiment the grating component may be a binary grating having a duty cycle of less than 0.5.

In an aspect of the first embodiment a ratio A over B of a diffraction order A among the different orders and a diffraction order B among the different orders may be smaller than 2. Wherein the grating component diffracts light of a first wavelength associated with the diffraction order A at the same angle as the grating component diffracts light of a second wavelength associated with the diffraction order B. Wherein, the first wavelength may be less than the second wavelength.

At least a second embodiment may be a system comprising a spectrally encoded endoscopy probe for color imaging. The probe may comprise: a light guiding component for guiding illumination light; a light focusing component, a grating component. Wherein, the light guiding component, the light focusing component and grating component may be configured such that a set of light beams of multiple wavelengths may be diffracted in different orders at a same angle. The set of light beams may include at least 3 light beams. Each light beam among the set of light beams may be associated with a different wavelength. The system may also comprise a second light guiding component for guiding collected light, at least one detector, and a processor. The processor may be adapted and configured to form a color image based on information from the light diffracted in the multiple orders.

In an aspect of the second embodiment at least one detector may comprise a spectrometer.

In an aspect of the second embodiment the multiple orders of spectrally dispersed light may be $-m$, $-(m+1)^{th}$, and $-(m+2)^{th}$ diffraction orders, and wherein m is an integer.

In an aspect of the second embodiment, the system may further comprise a beam block positioned outside the probe field of view to block light beams diffracted in orders which are not the multiple orders.

In an aspect of the second embodiment the second light guiding component may comprise one or more angle polished optical fibers.

In an aspect of the second embodiment may further comprise a scanner for scanning the set of light beams in a first direction. The processor may be further configured to apply a smoothing function with a kernel in the first direction to the information from the light diffracted in the multiple orders. The kernel is a first size for a first subset of wavelengths for each of the multiple orders. The kernel is a second size for a second subset of wavelengths for each of the multiple orders. The first size may be different from the first size.

In an aspect of the second embodiment, the color image may be a polar image. The first subset of wavelengths for each of the multiple orders may be associated with a first range of radii of the polar image. The second subset of wavelengths for each of the multiple orders may be associated with a second range of radii of the polar image. The first range of radii may be less than the second range of radii. The first size of the kernel may be larger than the second size of the kernel.

At least a third embodiment may be a system comprising a spectrally encoded endoscopy probe for color imaging. The probe may comprise: a light guiding component for guiding illumination light; a light collecting component that comprises a first grating, and a lens. The system may also comprise a second light guiding component for guiding collected light; at least one detector; and a processor. The processor may be adapted and configured to form a color image based on information from the collected light. The spectrally encoded endoscopy probe may be configured such that a set of collected light beams of multiple wavelengths are diffracted in different orders and coupled into the second light guiding component by the light collecting component. The set of collected light beams may include at least 3 light beams. Each light beam among the set of collected light beams may be associated with a different wavelength. The spectrally encoded endoscopy probe may be configured such that each of the collected light beams among the set of collected light beams that is coupled into the second light guiding component is diffracted by the first grating in a substantially single order.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 14 is an illustration of a portion of another embodiment.

FIGS. 17A-B are illustrations of segmentation of data that might be obtained by an embodiment.

Figure 1:
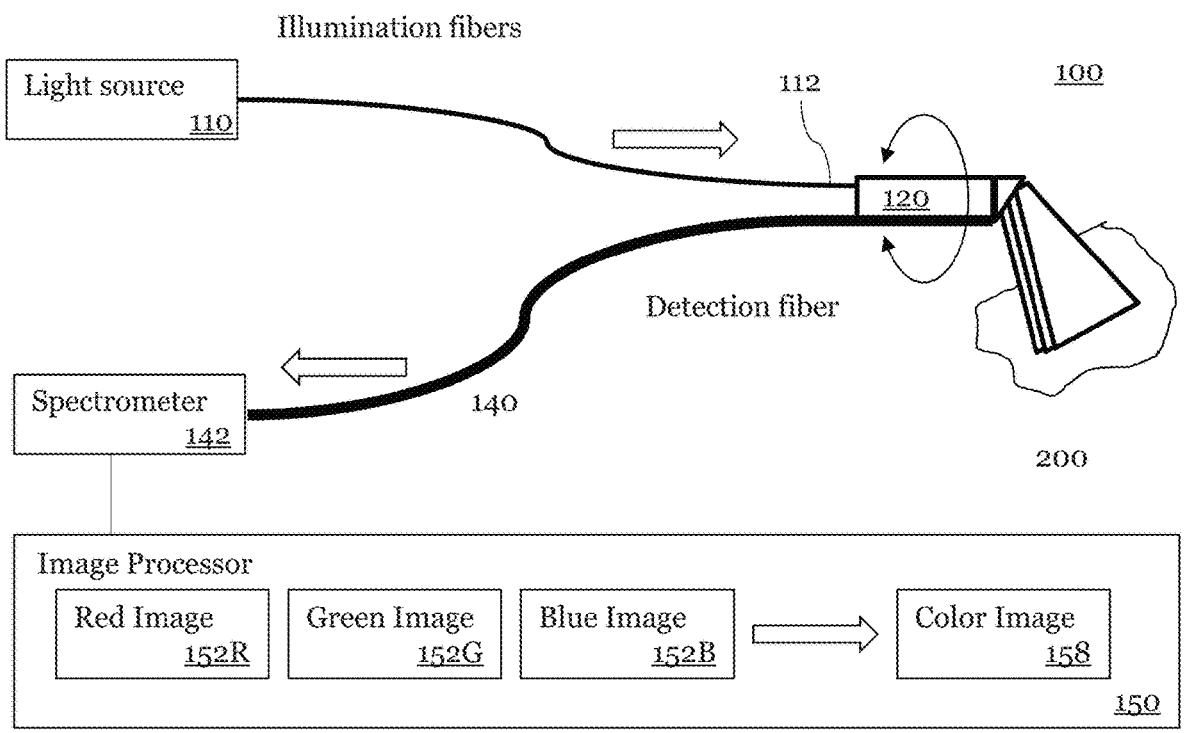
FIG. 1 is a diagram of an embodiment.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION

First Embodiment—Side View

An exemplary embodiment of a SEE probe system 100 according to the present disclosure is shown in FIG. 1. This exemplary SEE probe system 100 may include a light source 110, a probe 120, a spectrometer 142, and an image processor 150. In this embodiment, broadband light from the light source no is coupled into a light guiding component which may be an illumination optical fiber 112.

The broadband light has sufficient bandwidth to allow for spatial resolution along the spectrally dispersed dimension. In some embodiments, the broadband light is a broadband visible light sources that includes a blue band of light (including wavelength $\lambda_{B1}$ to $\lambda_{BN}$), a green band of light ($\lambda_{G1}$ to $\lambda_{GN}$), and a red band of light ($\lambda_{B1}$ to $\lambda_{RN}$). For example, the blue band contains 400-500 nm light, the green band contains 500-600 nm light, and the red band contains 600-800 nm. In other embodiments, the wavelengths of the broadband light are optimized for identifying specific features such as blood, tissue, etc., and may extend into the near-IR region, for example 1200 nm. In an embodiment, each wavelength band may have wavelength range that is greater than 30 nm. An embodiment may include at least three bands which would allow the SEE to produce color images. More bands may be used to acquire additional information.

The broadband light source no may include a plurality of light sources or may be a single light source. The broadband light source no may include one or more of a laser, an OLED, a LED, a halogen lamp, an incandescent lamp, supercontinuum light source pumped by a laser, and/or a fluorescent lamp. The broadband light source no may be any light source that provides light which can then be split up into at least three bands in which each band is further dispersed to provide light which is then used for spectral encoding of spatial information. The broadband light source no may be fiber coupled or may be free space coupled to another component of the SEE probe system 100.

The light guiding component may be an illumination fiber 112 or some other optical waveguide which is connected to an SEE probe 120. The illumination fiber 112 may be a single-mode fiber, multi-mode fiber, or a double clad fiber. Preferably, a single fiber is used as the illumination fiber 112. The probe 120 or parts thereof may be rotated or oscillated as indicated by the arrow. For example, the illumination fiber and illumination optics may be rotated via a Galvano motor.

Figure 2:
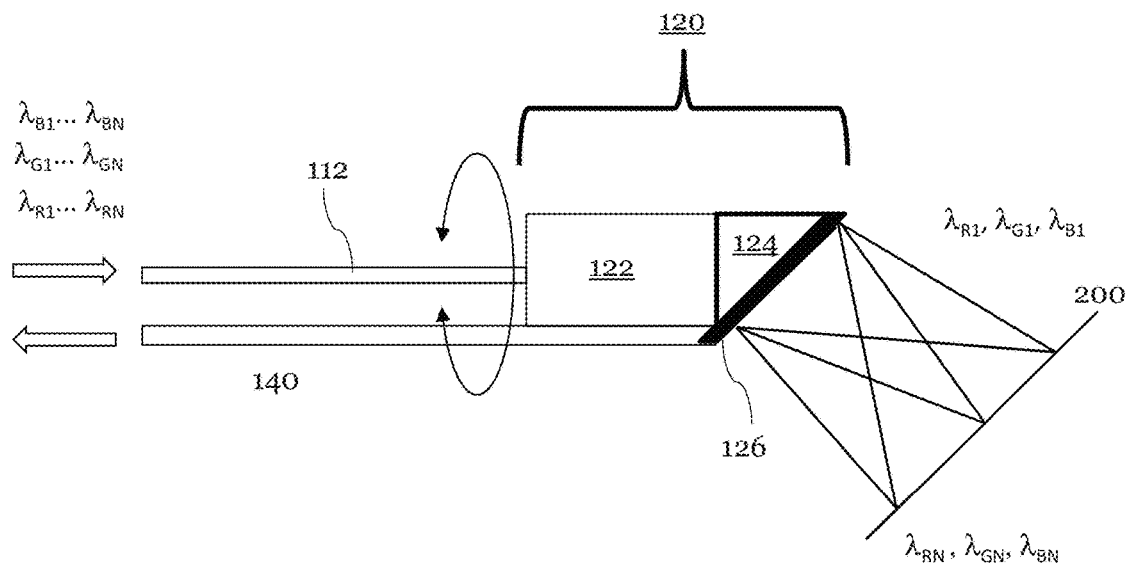
FIG. 2 schematic of a probe that may be used in an embodiment.

FIG. 2 is an illustration of a portion of the SEE probe system 100 showing a schematic of the probe 120 as it might be used in the embodiment illustrated in FIG. 1. This particular probe may be a side-view probe such that images from this probe will be reflected from a tissue or other imaged sample located to the side of and not directly in front of the probe. A light guiding component 112 (shown as an illumination fiber) transmits broadband light to the probe 120. A second light guiding component 140 (shown as a detection fiber) collects light from a sample 200. The probe 120 includes a light focusing component 122 and a grating component 126 which is shown attached to a spacer 124. The portion of the light focusing component 122 where the light guiding component 112 attaches is preferably a polished end of a lens. The second light guiding component 122 may be, for example, a GRIN lens or a ball lens and may be fixed to an angle-polished spacer 124. The spacer 124 may be made of, but is not limited to, glass, heat-curable resin, UV-curable resin, or plastic. The light guiding component 112 may be centered or off-centered from the second light guiding component 122. The second light guiding component 122 may be a light focusing component. In the centered case the light direction exiting the second light guiding component 122 is substantially parallel to optical axis of the second light guiding component 122. In the off-centered case the light direction exiting the second light guiding component 122 is at an angle relative to the optical axis of the second light guiding component 122 depending on the off-centered amount.

Figure 16:
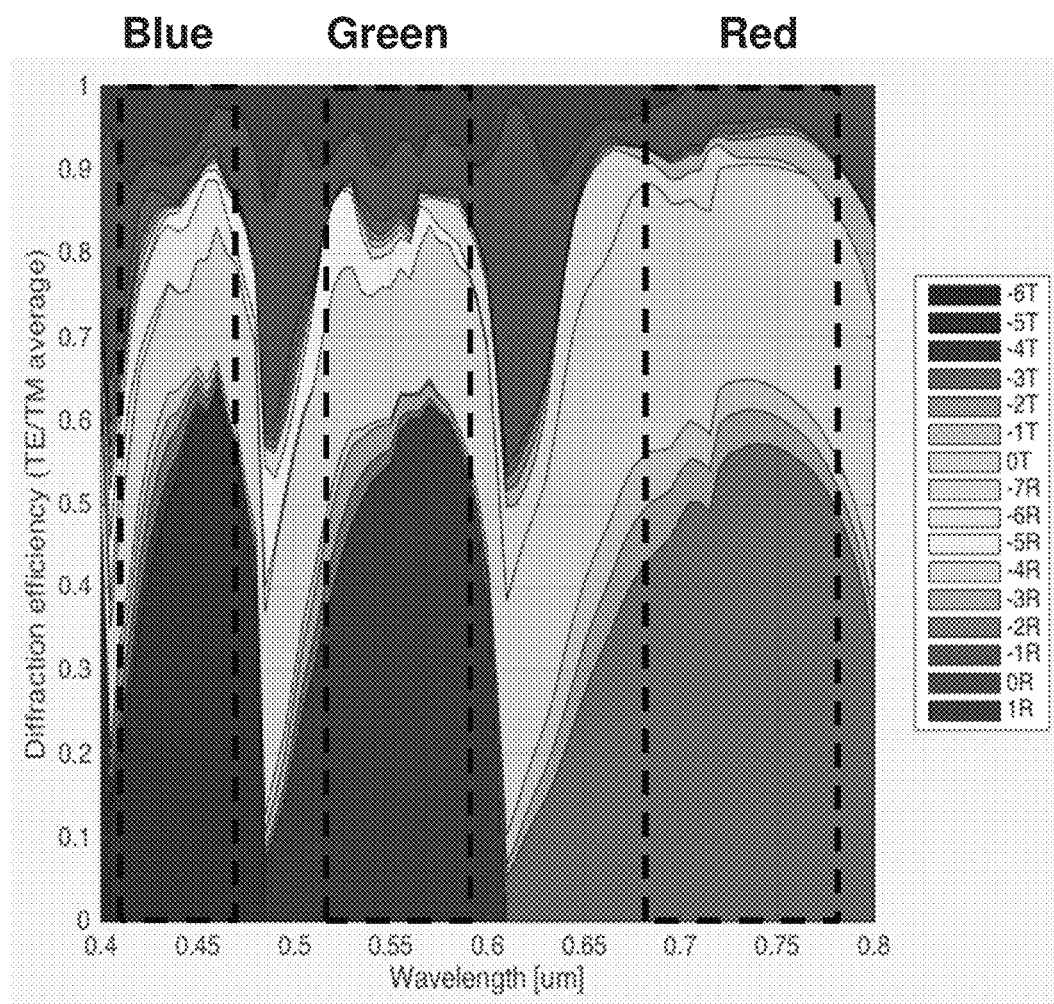
FIG. 16 is an illustration of diffraction power distributions for a component of an embodiment.

The grating 126 may be fabricated by techniques such as dry-etching, wet-etching, nano-imprint, and soft lithography. It may be formed directly on the spacer 124. For example, the spacer 124 with grating 126 may be fabricated by dicing and angle-polishing etched glass grating. The grating 126 may be, but is not limited to, a binary grating, a blazed grating, or a holographic grating. FIG. 16 is an illustration of simulation results for a diffraction power distribution across many diffraction orders for a grating 126 which may be used in an embodiment, where T and R in the legend stand for transmission and reflection, respectively.

Figure 3:
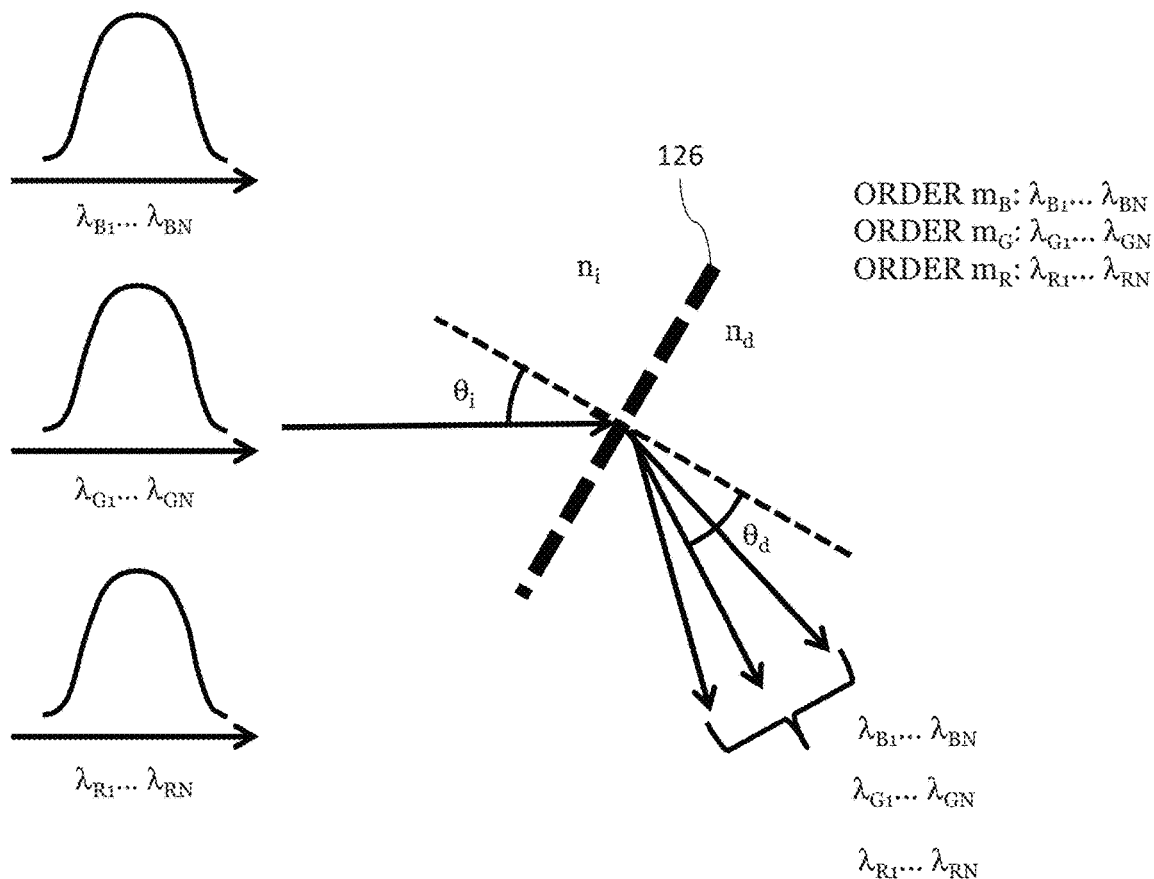
FIG. 3 is an illustration of light being diffracted in a portion of an embodiment.

A function of the grating 126 is illustrated by FIG. 3. The blue band of light ($\lambda_{B1}$ to $\lambda_{BN}$), the green band of light ($\lambda_{G1}$ to $\lambda_{GN}$), and red band of light ($\lambda_{R1}$ to $\lambda_{RN}$) are incident on the grating 126 at substantially the same incident angle $\theta_i$. The diffraction angle $\theta_d$ may be determined by the grating equation such as equation (1):

$$n_i \sin \theta_i + n_d \sin \theta_d = -mG\lambda \quad (1)$$

In which $n_i$ is representative of refractive index of the material on the incident side of the grating 126; $n_d$ is the refractive index of the material on the diffraction side of the grating; m is the diffraction order; G is spatial frequency of the grating 126, and $\lambda$ is wavelength of the light. In an exemplary embodiment, the diffraction conditions may be: $n_i=1.5037$; $n_d=1$; $\theta_i=42.81°$; and G=860/mm. In some embodiments, the grating 126 is designed so that the absolute value of the product of the spatial frequency G and the diffraction order for green light $m_G$, $|m_G G|$, is more than 2000/mm, 2500/mm, or 3000/mm. The inventors have determined that increasing $|m_G G|$ increases the field of view (FOV) for an embodiment. The FOV is an angular range of illumination angles associated with each wavelength bands which produce overlapping beams of light associated with each diffraction order.

It is understood that, while the red, green, and blue light are incident on the grating 126 at substantially the same incident angle $\theta_i$, there may be some differences due to dispersion. Wavelength shifts on the sample 200 due to those differences may be compensated for in image reconstruction process by the image processor 150, if necessary. For example, the incidence angle $\theta_i$ of the red light and the blue light may vary by 1.0° or less. Substantially in the context of the incident angle $\theta_i$ means variation of less than 2.0°, 1.0° or 0.5° depending on the dispersion properties of the optical components.

The grating 126 may be a binary grating whose duty cycle (opening width/period) is less than 0.5 allowing for high diffraction efficiency. The duty cycle may preferably be less than 0.4. The groove depth may be greater than 1 μm, preferably greater than 1.1 μm, or greater than 1.2 μm.

In order to make the blue band of illumination light, green band of illumination light, and red band of illumination light overlap on the sample 200, the diffraction order for the blue band of light $m_B$, the diffraction order for the green band of light $m_G$, and the diffraction order for the red band of light $m_R$ are restricted to satisfy equations (2) below:

$$|m_B| = |m_G| + 1$$

$$|m_R| = |m_G| - 1$$

$$\{m_R, m_G, m_B \in \mathbb{Z} \mid sgn(m_R) = sgn(m_G) = sgn(m_R), (m_R, m_G, m_B) \neq 0\} \quad (2)$$

In an embodiment, the light of 3 wavelengths ($\lambda_{BX}$, $\lambda_{GX}$, $\lambda_{RX}$) in which X is an integer from 1 to N representing the wavelengths in the blue, green and red wavelength bands are all incident on the grating 126 at substantially the same angle $\theta_i$ and are all diffracted at substantially the same angle $\theta_d$ the applicants have determined that this puts limitations on the edges of the wavelength bands such that the following set of equations (3) place conditions on the edges of the wavelength bands. In the context of the present disclosure diffracted at substantially the same angle $\theta_d$ means that edges of the wavelength bands are chosen such that the edges of each wavelength band have substantially the same diffraction angle, within 5, 4, 3, 2, or 1 pixel at the spectrometer 142, or, in some embodiments, within the measurement tolerance of the spectrometer 142. The edges of each wavelength band form a wavelength range which is diffracted at a specific angle range for a specific diffraction order. In the discussion above, any material dispersion from, for example, a GRIN lens or spacer, are not contemplated. Material dispersion from these and other optical elements may also affect the angle θ_d. However, it is contemplated that the effect of the material dispersion can be minimized or removed through a calibration step. Each wavelength band is chosen so that all wavelength bands have substantially the same angle range. In an embodiment, the angle range may be greater than 10°.

$$\lambda_{B1} = \frac{|m_G|}{|m_G| + 1} \lambda_{G1} \quad (3)$$

$$\lambda_{BN} = \frac{|m_G|}{|m_G| + 1} \lambda_{GN}$$

$$\lambda_{R1} = \frac{|m_G|}{|m_G| - 1} \lambda_{G1}$$

$$\lambda_{RN} = \frac{|m_G|}{|m_G| - 1} \lambda_{GN}$$

$$\lambda_{R1} > \lambda_{RN} > \lambda_{G1} > \lambda_{GN} > \lambda_{B1} > \lambda_{BN}$$

Preferably, the ratio of $m_B/m_R$ is smaller than 2 so that wavelength bands do not overlap on the sensor of the spectrometer 142.

Preferably, $m_G$ is equal to or smaller than −4 so that the overlap for three different wavelength bands (e.g., red, green, and blue wavelength, RGB) can be achieved inside the wavelength bandwidth of 400-800 nm. In some preferred embodiments, $m_G$ is −4, −5, or −6. In some preferred embodiments, the product of the absolute value of $m_G$ and G is greater than or equal to 2000/mm so as to achieve large field of view. Preferably, the product of the absolute value of $m_G$ and G is greater than or equal to 2500/mm, 3000/mm, or more. However, other embodiments where the different wavelengths are less than 400 nm or greater than 800 nm may also be used. In an embodiment, in which the bandwidth of all the overlapping bands is between 400 nm and 800 nm, a minimum value for an absolute value of the different diffraction orders is 3. In an embodiment, in which the bandwidth of all the overlapping bands is between 400 nm and 1200 nm, a minimum value for an absolute value of the different diffraction orders is 2.

Table 1 shows some exemplary diffraction orders and red green and blue wavelength ranges.

TABLE 1

|  | Example 1 | Example 2 | Example 3 |
| --- | --- | --- | --- |
| ($m_B$, $m_G$, $m_R$) | (−5, −4, −3) or (5, 4, 3) | (−6, −5, −4) or (6, 5, 4) | (−7, −6, −5) or (7, 6, 5) |
| ($\lambda_{B1}$-$\lambda_{BN}$) | (408 nm-468 nm) | (417 nm-479 nm) | (437 nm-489 nm) |
| ($\lambda_{G1}$-$\lambda_{GN}$) | (510 nm-585 nm) | (500 nm-575 nm) | (515 nm-570 nm) |
| ($\lambda_{R1}$-$\lambda_{RN}$) | (680 nm-780 nm) | (625 nm-719 nm) | (612 nm-684 nm) |

Figure 13A:
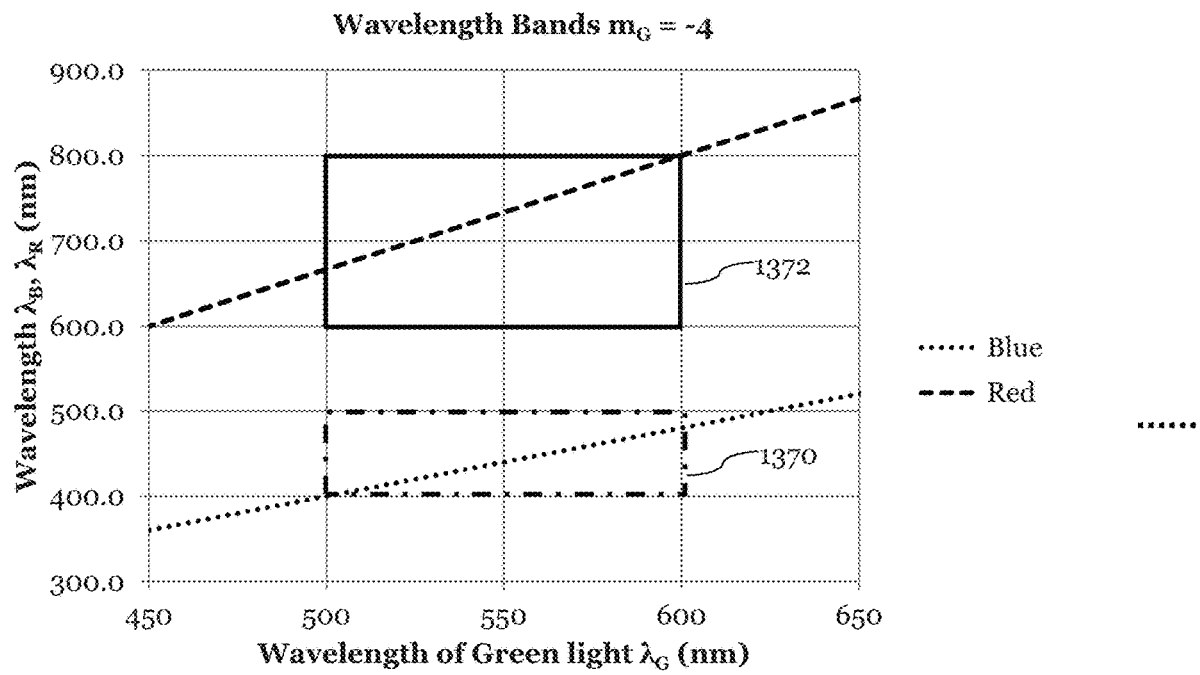
FIGS. 13A-F are illustrations of the bandwidth overlaps of the different channels.
Figure 13B:
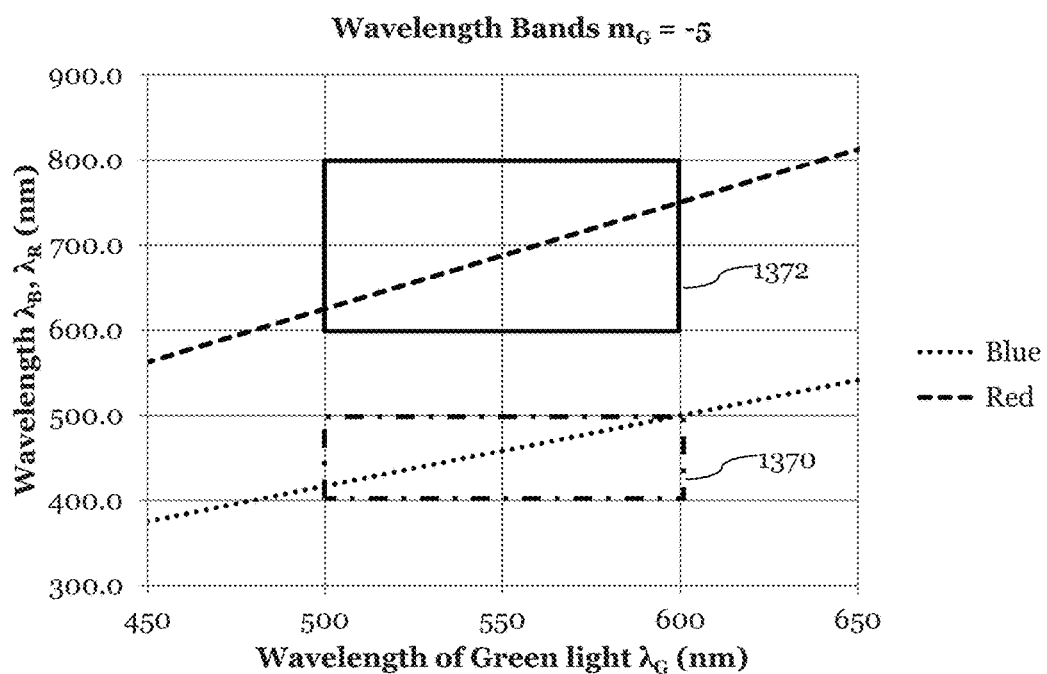
Figure 13C:
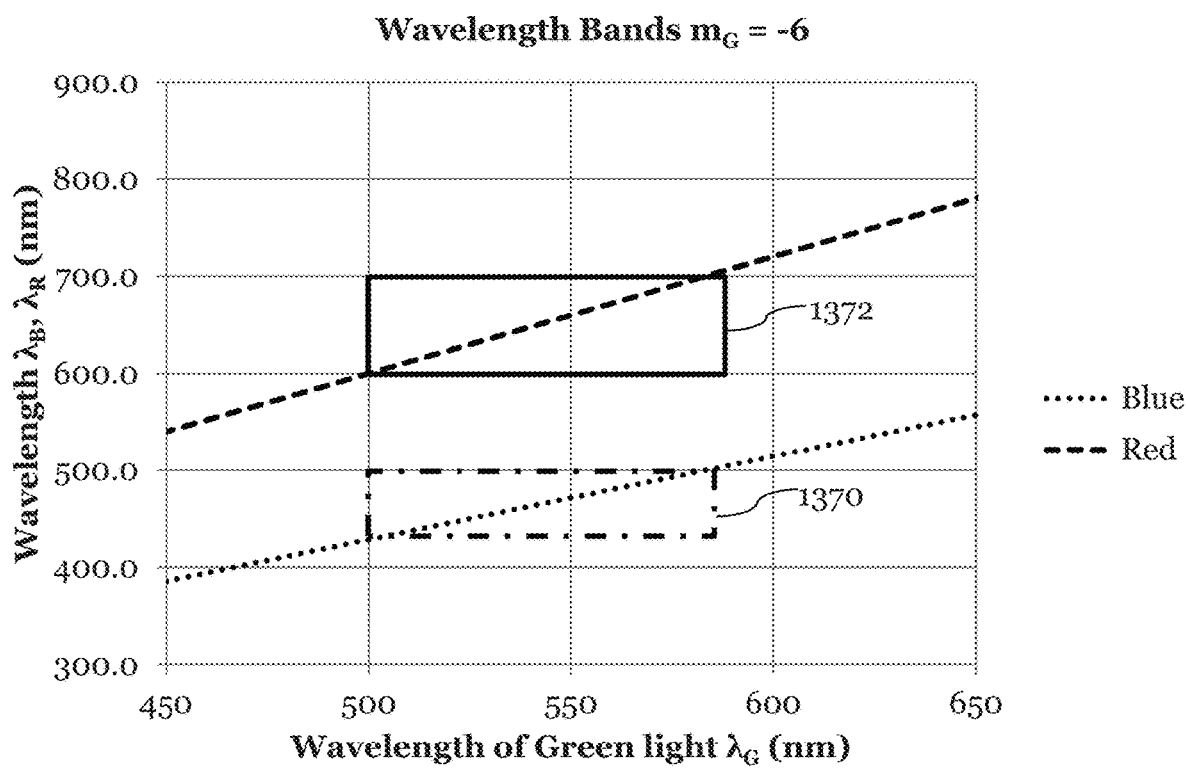
Figure 13D:
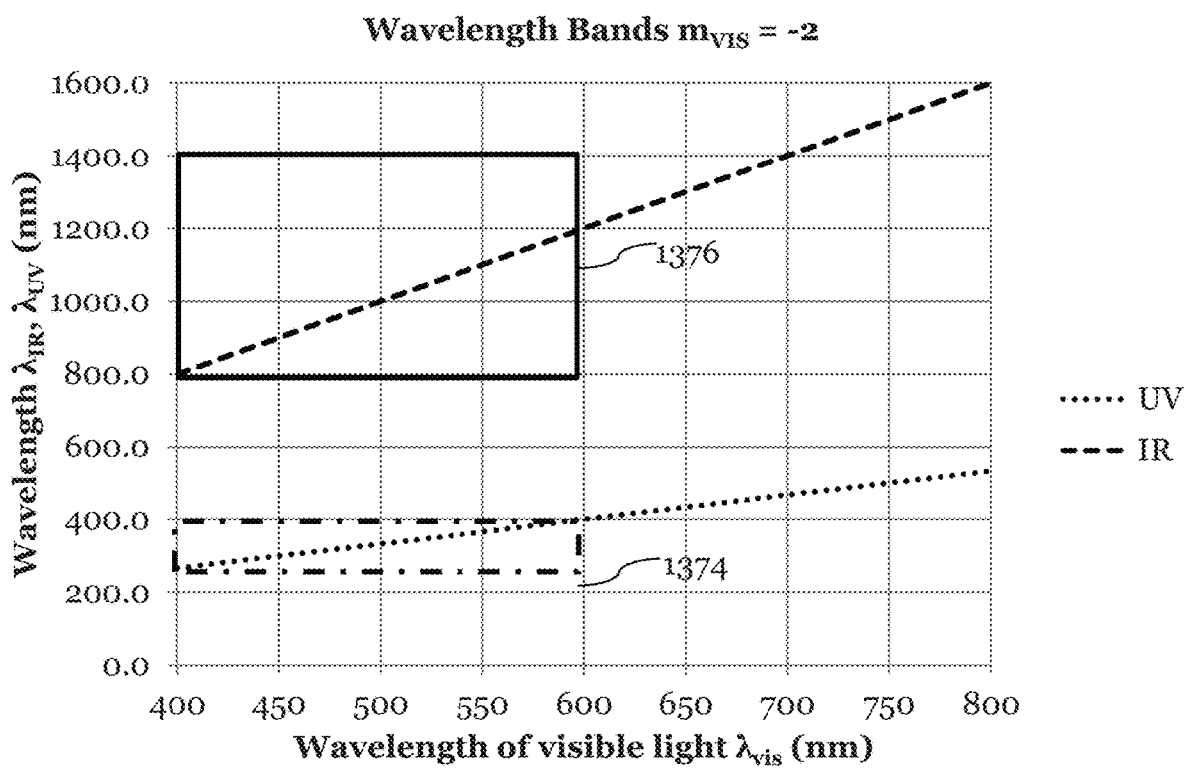
Figure 13E:
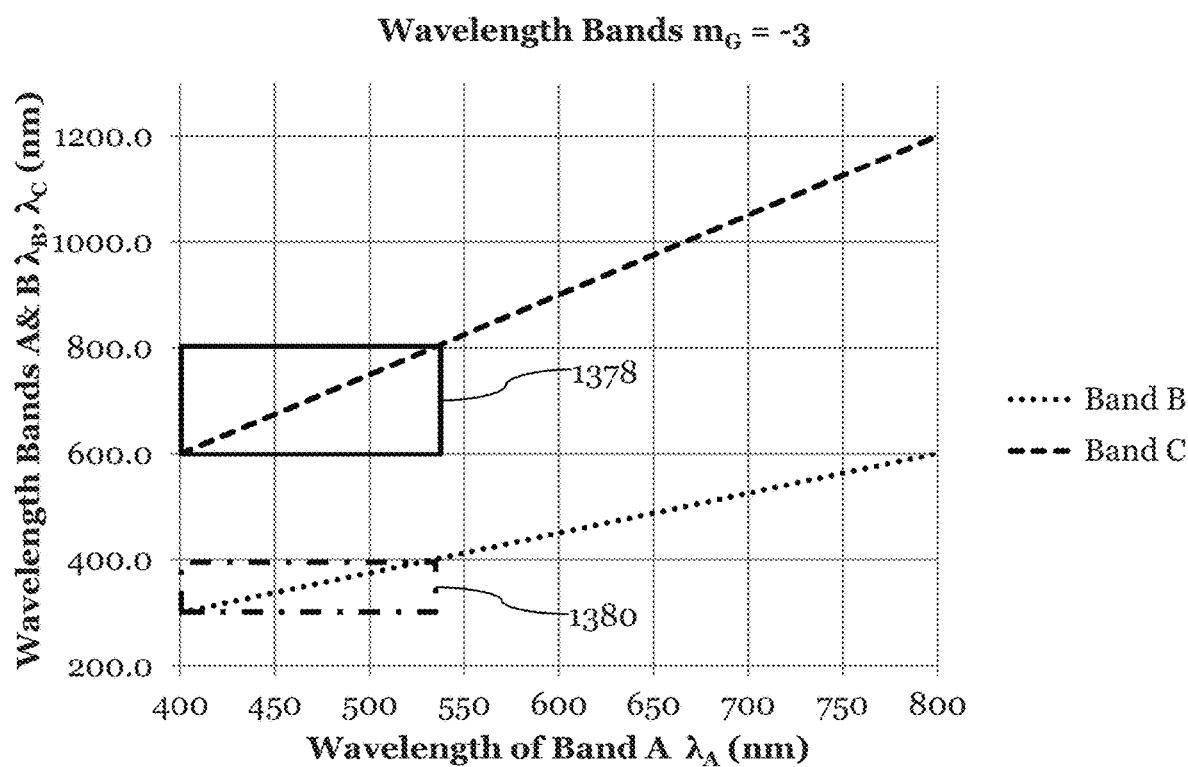
Figure 13F:
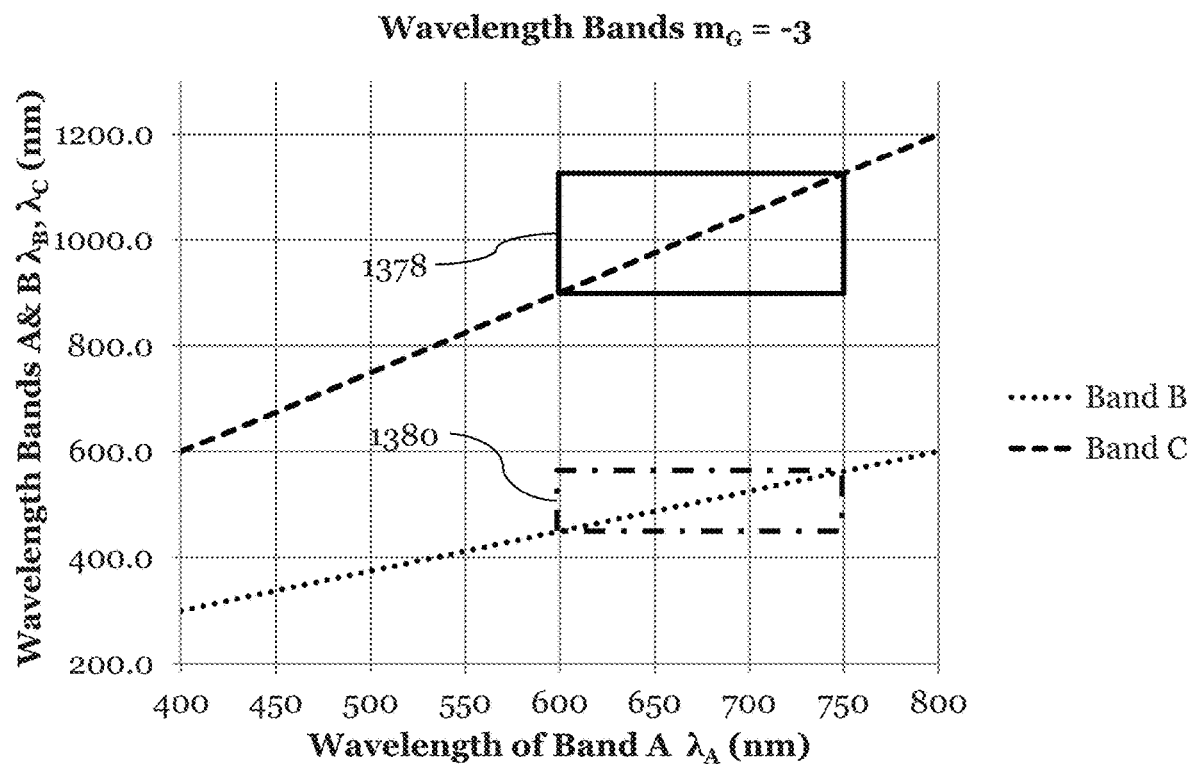

FIG. 13A is an illustration of Example 1 in which equation (3) has been plotted to illustrate the overlap of the green light and the blue light as bounded by the bandwidth box 1370 when $m_G$ is equal to −4. FIG. 13A also illustrates the overlap of the green light and the red light as bounded by the bandwidth box 1372 when $m_G$ is equal to −4. FIG. 13B is an illustration of example 2 in which equation (3) has been plotted to illustrate the overlap of green, blue, and red light in a similar manner to FIG. 13A except that $m_G$ is equal to −5. FIG. 13C is an illustration of example 3 in which equation (3) has been plotted to illustrate the overlap of green, blue, and red light in a similar manner to FIG. 13A except that $m_G$ is equal to −6. FIG. 13D is an illustration of an embodiment in which UV, IR, and visible light are used in which the bandwidth box 1374 illustrates the overlap of the UV and visible light and bandwidth box 1376 illustrates the overlap of the IR and the visible light. FIGS. 13E-F are illustrations of embodiments in which an arbitrary wavelength bands A, B, and C are used. Bandwidth boxes 1378 and 1380 illustrate the overlap of wavelength bands.

After illumination of the diffracted light (e.g., red, green, and blue light) on the sample 200 (e.g., a tissue or in vivo sample), light is reflected, scattered, photoluminescence by the sample 200. This light is collected by the detection fiber 140 through the grating 126 (see FIG. 2). In an alternative embodiment, the light collected by the detection fiber 140 does not pass through the grating 126.

Detection fiber(s) 140 used to collect the light may be attached on or near the side surface of the lens 122. The detection fiber 140 may be a single-mode fiber, multi-mode fiber or double clad fiber. In this particular embodiment, the grating 126 is attached to both the spacer 124 and the detection fiber 140. However, in other embodiments, the detection fiber(s) are not attached to the grating 126. The detection fiber 140 may optionally be rotated along with the illumination optics or may be stationary. If rotated, the detection fiber 140 may be connected, via a rotary junction, to a second non-rotating detection fiber.

As shown in FIG. 1, the collected light is delivered to the spectrometer 142 via the detection fiber 140. The spectrometer 142 obtains 1D spectral data for the 3 wavelength bands (e.g., blue, green, and red light). This 1D spectral data corresponds to information from the three illumination lines (RGB) on sample 200.

The probe 120 of FIG. 1 is rotated around the optical axis by a motor as indicated by the arrow such that illumination light lines scan the sample, and 2D data (wavelength and time) may be obtained by the spectrometer 142. The motor can be, for example, a Galvano motor, stepping motor, a piezo-electric motor, or a DC motor. A rotary junction may be used for rotation of the probe. For example, by rotating the spectrally encoded lines in the direction of the arrow, a circular region can be imaged. This circular region can be located approximately perpendicular to the SEE probe, and therefore, the exemplary SEE probe shown in FIG. 1 can conduct forward-view imaging if m and G are chosen so that light is diffracted at angle of $\theta_d = \theta_i$. Alternatively, the probe 120 may be oscillated to provide similar 2D data. At the spectrometer 142, the wavelength of the collected light can be read out, which can be used to generate a line image of the sample.

After the spectrometer and one or more detectors detects the collected light, an image processor 150 generates three 2D images (152R, 152B, 152G) for red, green, and blue from the data. In other embodiments, two, four, or more 2D images are formed using a probe with appropriate overlapping orders of diffracted light.

The image processor 150 builds a 2D color image 158 from the 3 substantially monochromatic images: a red image 152R; a green image 152G, and a blue image 152B. This color image 158 may be created so as to simulate a true color image or may be adjusted to highlight differences in, for example, tissue type. In some embodiments, a two or four tone image may be built instead of or in addition to the color image 158.

A color calibration process may be applied when the three substantially monochromatic images (152R, 152G, 152B) are created and combined into 2D color image 158 by the processor 150.

An embodiment may use a method for color calibration that makes use of reference spectra for three wavelength bands (red, green, and blue) and their reference RGB values. The reference RGB values may be set for the 3 spectra. Those are pixel values that a target image may have in an RGB monitor when spectrum data obtained by SEE system from the target are identical to the reference spectra.

The first step of the method is to define a reference spectra ($I^{Reference}_X(\lambda)$) in which X is R, G, or B. For example, the reference spectra may be an average of spectrum data sets obtained by the SEE system 100 from the sample 200 itself. In another embodiment, reference spectra can be spectrum data obtained by SEE system 100 from another uniform tissue, a reference sample, or an artificial tissue sample. In yet still another embodiment, reference spectra may be created by multiplying spectrum data of a white calibration chart obtained by the SEE system and reflection spectrum data of the tissue of interest.

A second step may be to define reference RGB values ($v^{Reference}_X$) corresponding to the reference spectra. For example, if reference spectra are generated from tissue which looks white, reference RGB values can be something like (255, 255, 255) or (200, 200, 200) for 8-bit values. If the reference spectrum is generated from a tissue which looks pink, reference RGB values may be something like (250, 100, 180) for 8-bit values.

A third step may be to normalize the three substantially monochromatic images ($I^{Measured}_X(\lambda)$) and assign RGB values ($v^{Calibrated}_X(\lambda)$) with corresponding (i.e. red, green, or blue) one of the reference spectra and RGB values as illustrated in equation (4) below.

$$v^{Calibrated}_X(\lambda) = \frac{I^{Measured}_X(\lambda)}{I^{Referece}_X(\lambda)} v^{Reference}_X \qquad (4)$$

This is linear process, so it can be done either before or after the coordinate system conversion process (e.g. Polar to Cartesian). A fourth step may be to combine the 3 calibrated images into the 2D color image 158. A gamma correction process may be applied after the color calibration process.

In forward-view imaging, obtained 2D data (wavelength and time) can be converted to a 2D image through changing the coordinate system from a polar coordinate system to a Cartesian coordinate system. In one embodiment, the wavelength may be converted to a radius in polar coordinate system which is then converted to the Cartesian coordinate system.

Figure 5:
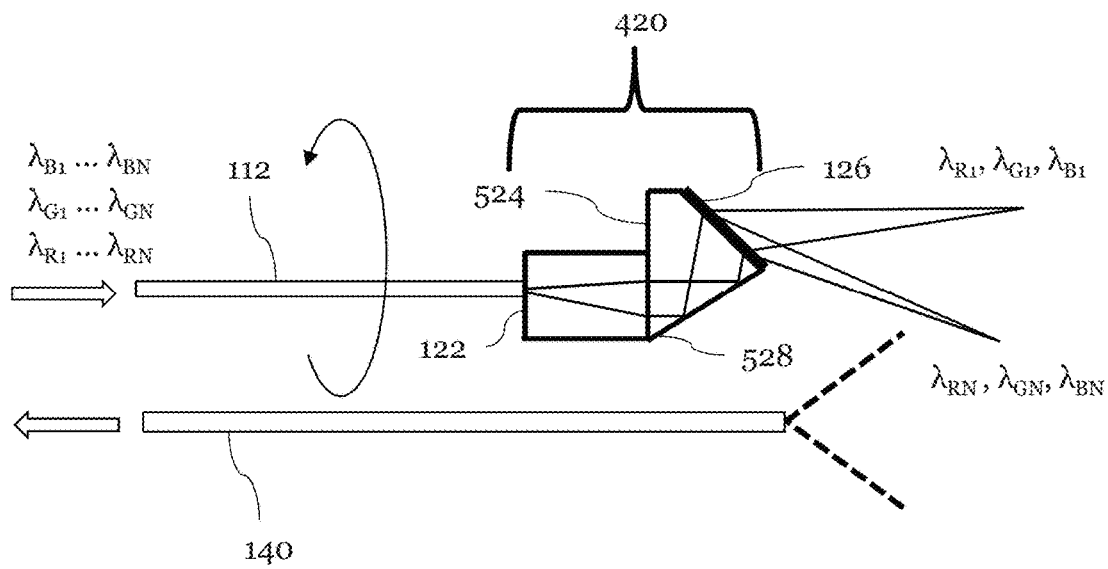
FIG. 5 shows schematic of a portion of an embodiment.

When obtaining a 2D polar image 1758 as illustrated in FIG. 17A, a shorter radius area (small view angle area, FOV center, 1754 in FIG. 17A) may be oversampled in a tangential direction compared to a longer-radius area (large view angle area, FOV edge, 1756 in FIG. 17A). In an embodiment, when the radius of the polar image 1758 is between zero and a first threshold, the number of data points which are gathered in the angular direction may be a first number which is greater than a second number. The second number being the number of data points which are gathered in the angular direction when the radius of the polar image 1758 is between a second threshold and a third threshold. The second and third threshold both being larger than the first threshold. Therefore, it may be effective to apply a smoothing function to the each 2D data of color spectrum band (e.g. R, G, B) which is taken by line-sensor spectrometer 142 before the coordinate system conversion with different kernel sizes depending on radius (larger size kernel for smaller radius) to increase SNR. For example, if the shortest wavelengths of the color spectrum bands is at the center of the FOV as illustrated in FIG. 5, it is efficient to apply a smoothing function with a larger kernel along the scan angle direction to a data subset 1792 (shorter wavelengths) than to data subset 1794 (longer wavelengths) in spectrometer data 1790 for each spectrum band as illustrated in FIG. 17B.

Figure 15A:
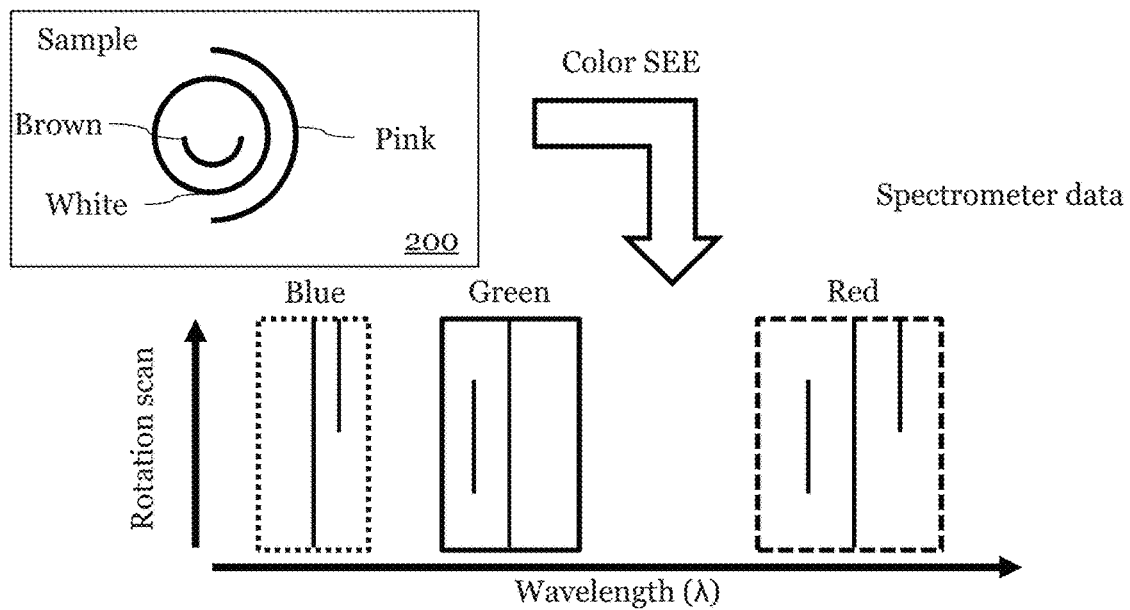
FIGS. 15A-C are illustrations of data that might be obtained by an embodiment.
Figure 15B:
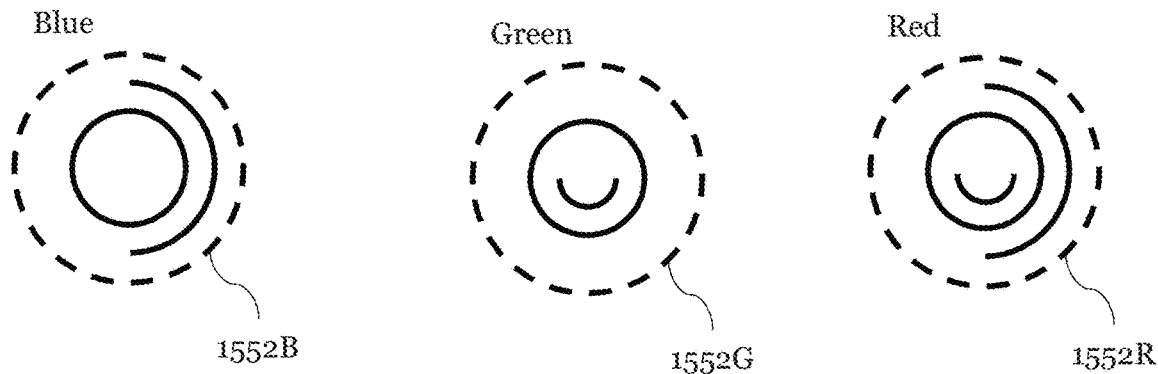
Figure 15C:
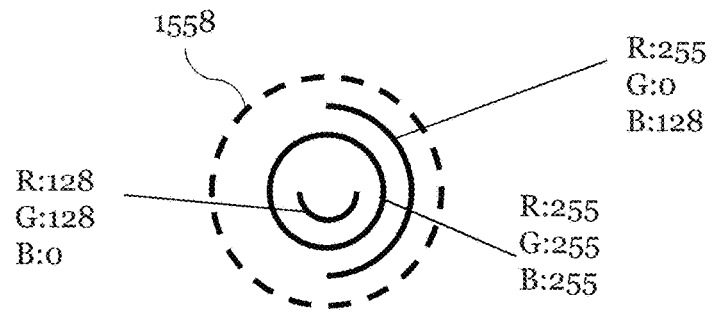

FIGS. 15A-C are illustrations of exemplary data that might be obtained by an embodiment. As illustrated in FIG. 15A, a sample 200 may include an inner brown half circle a central white circle, and a pink outer circle. The SEE probe collects light from the sample 200 and sends it the spectrometer 142 which produces spectrometer data as illustrated by the graph illustrated data each wavelength band obtains about each curve.

The spectrometer data is sent to the image processor 150. The image processor 150 produces the red image 152R, the green image 152G, and the blue image 152B as illustrated in FIG. 15B. The image processor 150 then combines the red image 152R, the green image 152G, and the blue image 152B to produce a color image 1558 as illustrated in FIG. 15C

Multiple spectrometers may be used as a spectrometer 142. For example, blue and green collected light may be delivered to one spectrometer, and red light to another spectrometer. Similarly, multiple detectors (not shown) may detect the light from the multiple spectrometers. The multiple spectrometers may share one or more components.

Second Embodiment—Forward View

Figure 4:
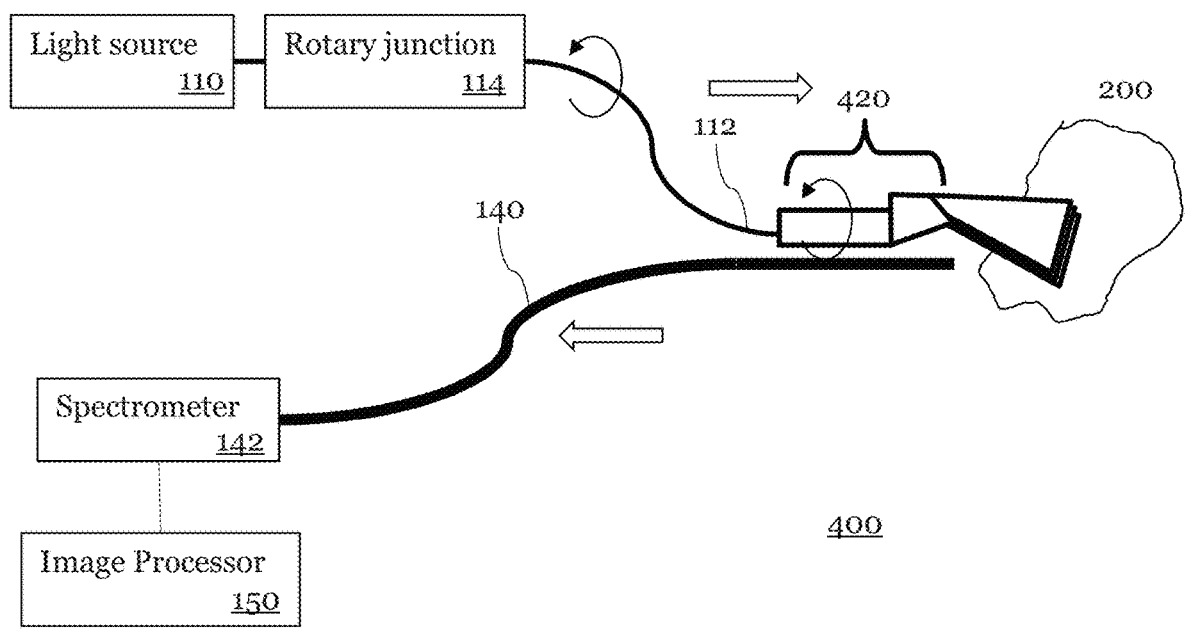
FIG. 4 is a diagram of another embodiment.

FIG. 4 is an illustration of a forward viewing SEE probe system 400 in which an embodiment may be implemented. The forward view SEE probe system also illustrates the use of a rotary junction 114 between the light source no and the probe 420.

As shown in FIG. 5, a light guiding component 112 (shown as an illumination fiber) transmits broadband light to the probe 120. A second light guiding component 140 (shown as a detection fiber) collects light. The probe 420 includes a light focusing component 122 and a grating component 126 which is shown attached to a spacer 524. The spacer has a mirror surface 528. The mirror 528 may be achieved, for example, by a reflective coating, a metal coating, or by using total internal reflection. The light guiding component 122 may be, for example, a GRIN lens or a ball lens and is fixed to an angle-polished spacer 524. The spacer 524 may be made of, but is not limited to, glass, heat-curable resin, UV-curable resin, or plastic.

As shown, light delivered thorough the illumination fiber 112 is slightly focused by the lens 122, reflected by the surface 528, and diffracted by the grating 126. The shortest wavelength light in each color bandwidth, ($\lambda_{R1}, \lambda_{G1}, \lambda_{B1}$), is diffracted to the sample 200 in the forward-view direction.

The detection fiber 140 collects light reflected the 200 sample. The detection fiber 140 may be one or more multi-mode fibers. The multiple fibers may be, for example, arrayed around the lens 122 and spacer 524. In some embodiments, there are 4, 5, 6, 7, 8, or more detection fibers 140. In some embodiments, the array of detection fibers 140 may have a "hole" at one or more positions to accommodate other optical or mechanical components such as a flushing means. The detection fiber(s) 140 may be stationary or rotate along with the lens 122 and spacer 524 together. Preferably, the detection fiber(s) 140 has a high NA. The NA may be more than 0.2 (more preferably . . . 0.3, 0.4, 0.5, 0.6).

Figure 6:
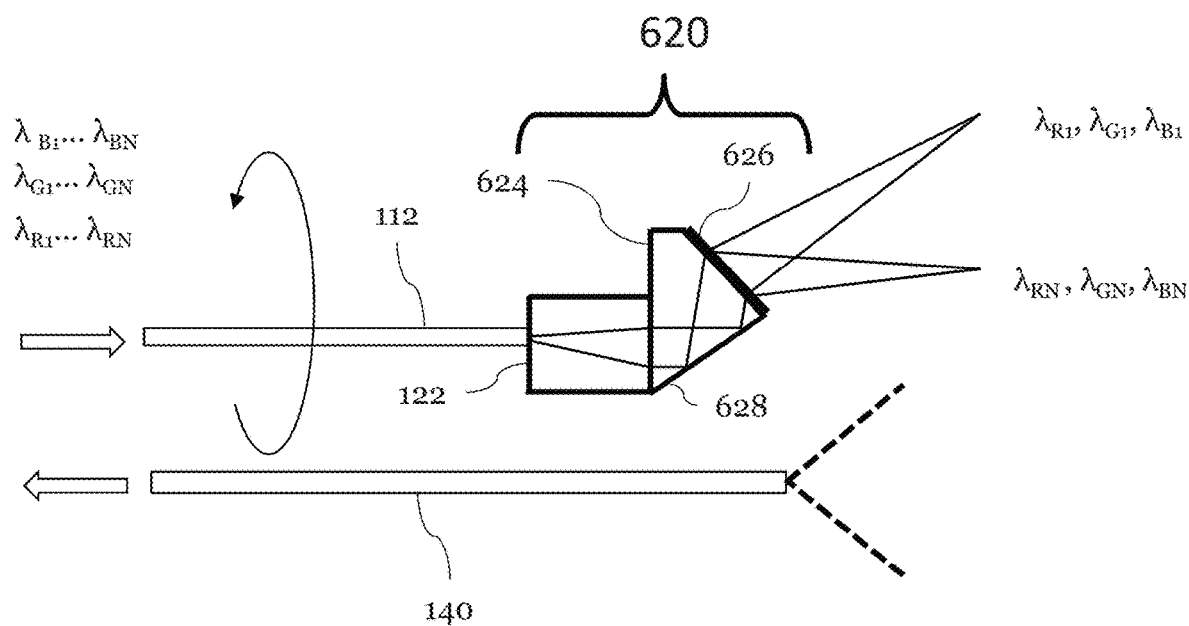
FIG. 6 shows schematic of a portion of another embodiment.

FIG. 6 is an illustration of another embodiment of an exemplary forward viewing SEE probe 620 which is substantially similar to the forward viewing probe 420 illustrated in FIG. 5 except that the grating 626 is used and the viewing area is shifted in accordance with the parameters of the new diffraction grating 626. Also, the spacer 624 is optimized so that the incident angle of the light from the surface 628 is optimized. In this design, grating parameters (refractive index, spatial frequency, and incident angle) and the angle are optimized so that the longest wavelength light in each color bandwidth, ($\lambda_{RN}, \lambda_{GN}, \lambda_{BN}$), is diffracted to the sample 200 in the forward-view direction.

The next highest diffraction order which is not used for imaging ($m_B-1$), may introduce noise into the system. In one embodiment, (e.g. $m_B=-6$) the diffraction angle for this higher order band which is not used is greater than maximum angle so that light is diffracted outside of field of view of probe detection optics, and it does not contribute substantially to the noise of the system. Preferably, the following condition described by equation (5) is satisfied so that the diffraction in the next highest order does not substantially occur.

$$\frac{-(m_B-1)G\lambda_{B1} - n_i\sin\theta_i}{n_d} > 1 \qquad (5)$$

In an embodiment, the grating 626 may be optimized so that the diffraction efficiency for illumination is higher than that in adjacent diffraction orders. For example, In one embodiment, $n_i=1.5037$, $n_d=1$, $\theta_i=42.81°$, G=860/mm, groove depth=1.45 um, and duty cycle=0.16. The diffraction efficiencies for the field of view (FOV) center and FOV edge is listed in table 2 below. Table 2A also illustrates the diffraction efficiency for the wavelengths which are the same at the FOV edge but in an adjacent order. Here the diffraction efficiency in the table is average of TE and TM diffraction efficiency. Diffraction efficiency is not zero between FOV center wavelength and FOV edge wavelength in each channel (Blue, Green, Red). In an embodiment, when the incident angle $\theta_i$ is greater than a critical angle for total internal reflection (TIR) than there is substantially no transmitted light associated with the zeroth order (m=0) of transmission for the grating while the light diffracted by the grating of the higher does pass through the grating.

TABLE 2A

| | Diffraction efficiency | | |
|---|---|---|---|
| | FOV center wavelength/ order | FOV edge wavelength/ order | Wavelength same as FOV edge in adjacent order |
| Blue | 10.1% (408 nm/-5th) | 27.4% (468 nm/-5th) | 0.4% (468 nm/-4th) |
| Green | 19.9% (510 nm/-4th) | 24.8% (585 nm/-4th) | 1.6% (585 nm/-3rd) |
| Red | 24.4% (680 nm/-3rd) | 18.5% (780 nm/-3rd) | 3.6% (780 nm/-2nd) |

In an embodiment, the grating 626 may be optimized so that the diffraction efficiency for illumination is higher than that in adjacent diffraction orders. For example, In one embodiment, $n_i=1.5037$, $n_d=1$, $\theta_i=38.67°$, G=800/mm, groove depth=1.7 um, and duty cycle=0.2. The diffraction efficiencies for the field of view (FOV) center and FOV edge is listed in table 2B below. Table 2B also illustrates the diffraction efficiency for the wavelengths which are the same at the FOV edge but in an adjacent order.

TABLE 2B

| | Diffraction efficiency | | |
|---|---|---|---|
| | FOV center wavelength/ order | FOV edge wavelength/ order | Wavelength same as FOV edge in adjacent order |
| Blue | 18% (408 nm/-5th) | 56% (468 nm/-5th) | 1.3% (468 nm/-4th) |
| Green | 30% (510 nm/-4th) | 57% (585 nm/-4th) | 0.7% (585 nm/-3rd) |
| Red | 42% (680 nm/-3rd) | 50% (780 nm/-3rd) | 3.0% (780 nm/-2nd) |

In an embodiment, the grating 626 may be optimized so that the diffraction efficiency is optimized for -6th/-5th/-4th orders for blue (415-475 nm)/green (498-570 nm)/red (622.5-712.5 nm), respectively. For example, in one embodiment, $n_i=1.5037$, $n_d=1$, $\theta_i=36.0°$, G=650/mm, groove depth=1.8 um, and duty cycle=0.25.

Figure 7:
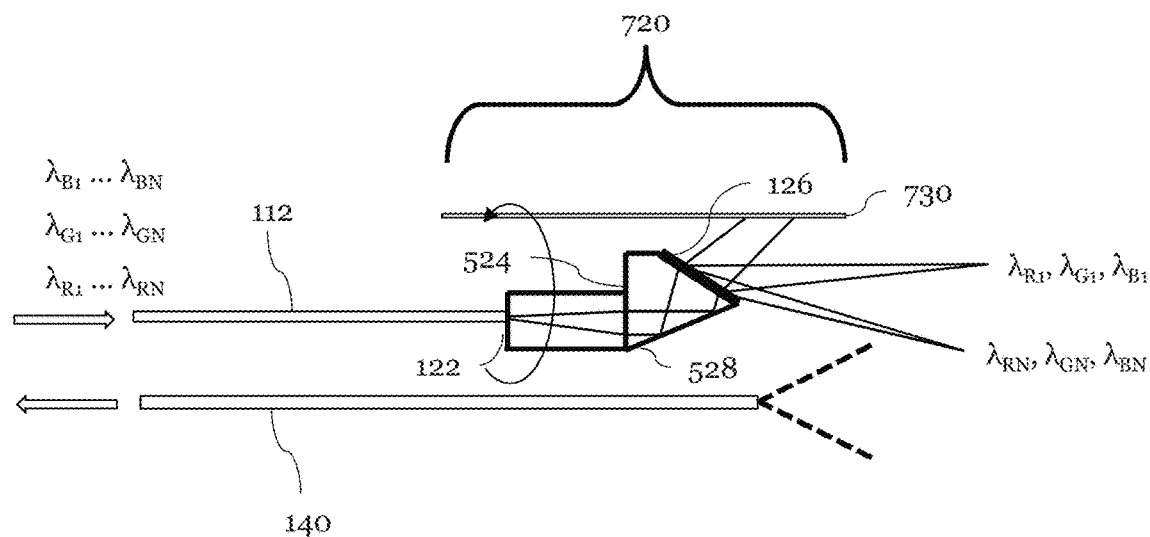
FIG. 7 shows schematic of a portion of another embodiment.

Yet another exemplary embodiment for a forward viewing SEE probe 720 is illustrated in FIG. 7 and is substantially similar to the SEE probe illustrated previously. The probe 720 further comprises a beam block 730. The beam block 730 is positioned around the grating 126 such that it blocks light which is diffracted at angles other than those in the field of view which is of interest. For example, the beam block 730 may block other orders whose diffraction angle is smaller than the diffracted light which illuminates the sample 200. The beam block 730 may absorb, reflect, or scatter such light. The beam block 730 may be tubing and may be stationary. The beam block 730 may rotate together with probe 120.

Figure 8:
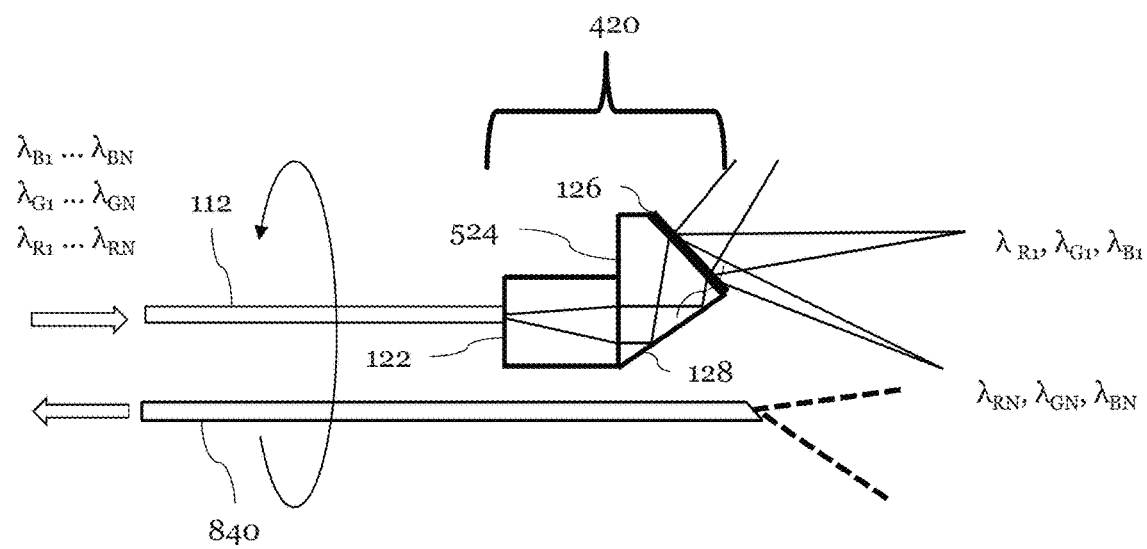
FIG. 8 shows schematic of a portion of another embodiment.

Yet another exemplary embodiment for a forward viewing SEE probe 420 is illustrated in FIG. 8. In this embodiment, a detection fiber 840 has an angle polished distal end so that acceptance angle is asymmetric and it does not collect light other than a specific field of view which is associated with specific order of the diffracted light. For example, light diffracted in other orders whose diffraction angle is smaller than the specific illumination light which is diffracted onto the sample 200. In an alternative embodiment, instead of having angle-polished distal end, the detection fiber 840 may have a prism on the distal end. Also exemplified in this embodiment is a detection fiber 840 that is rotating along with the illumination fiber 112, lens 122, and spacer 524.

Figure 9:
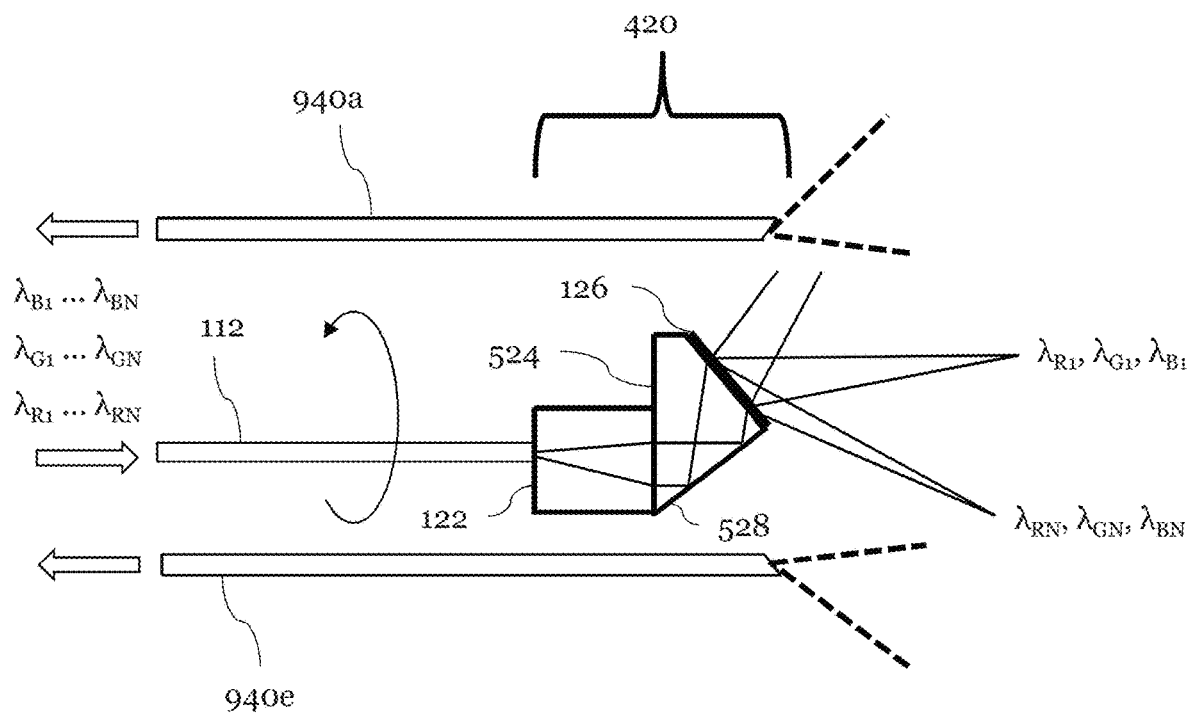
FIG. 9 is an illustration of a profile of a portion of another embodiment with multiple detection fibers.
Figure 10:
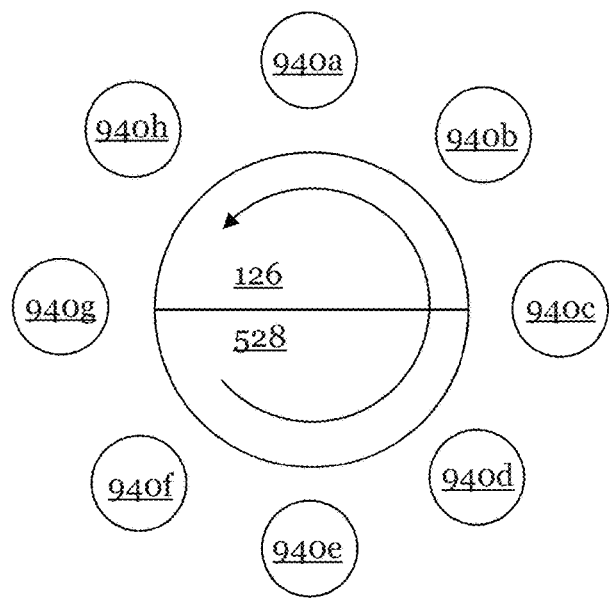
FIG. 10 is an illustration of a front-view of a portion of another embodiment with multiple detection fibers.

FIGS. 9-10 are illustration of an embodiment in which the detection fiber comprises multiple detections fiber 940a-z forming a fiber bundle 940. The detection fibers 940a-z may include multiple fibers arrayed around the spacer 524 and the grating 126 as illustrated in FIGS. 9-10. As shown in FIGS. 9-10 an exemplary probe 420 is surrounded with multiple (8 in this example) detection fibers 940a-z. Light from each of the detection fibers may be used together or selectively in image processing by the image processor 150. A time gate may be used to select which detection fiber or fibers is used. This may be done, for example, by a 2D camera with time-gated exposure or with Galvo scanner and a line camera.

FIG. 14 is an illustration of how a single spectrometer 1442 may be adapted to gather data from the multiple fibers of the fiber bundle 940. As shown in FIG. 14 individual fibers of the fiber bundle 940 on the input side 1440a of the fiber bundle 940 may form a ring. The ring shape is exemplary and other shapes may be used for the input side of the fiber bundle such as a polygon, ellipse, or other shapes. While an output side 1440b, of the fiber bundle may form an array such as with a fiber ribbon.

The spectrometer 1442 may include a collimating lens 1482 for gathering light from the output side 1440b. The collimating lens 1482 may be a single lens, a lens set, or a lens array. The lens array may include a single lens for each fiber in the fiber bundle 940. The collimating lens 1482 may substantially collimate the light from the output side 1440b.

The collimating lens 1482 along with one or optical components such as mirrors and polarizers may guide the light to an optically dispersive component 1484 such as one or more gratings or prisms. The optically dispersive component 1484 disperses the light as illustrated in FIG. 14. In FIG. 14 the blue light is shown with dotted lines, green light is shown with solid lines, and red light is shown with dashed lines.

The spectrally dispersed light may then be focused by a focusing lens 1486. The focusing lens 1486 may be a single lens, a lens set, or a lens array. The focusing lens 1486 may then focus the spectrally dispersed light onto a sensor array 1442. Each pixel in the sensor array 1488 may be a rectangular pixel 24 μm×500 μm. Each pixel may be a logical pixel made up of a plurality of smaller square pixels in a standard sensor array 144. If the focusing lens 1486 is a lens array then the lens array may include a lens for each rectangular pixel. The sensor array 1488 can produce an image in which spectral information is along a first axis and spatial information from each fiber is along a second axis orthogonal to the first axis.

Figure 11:
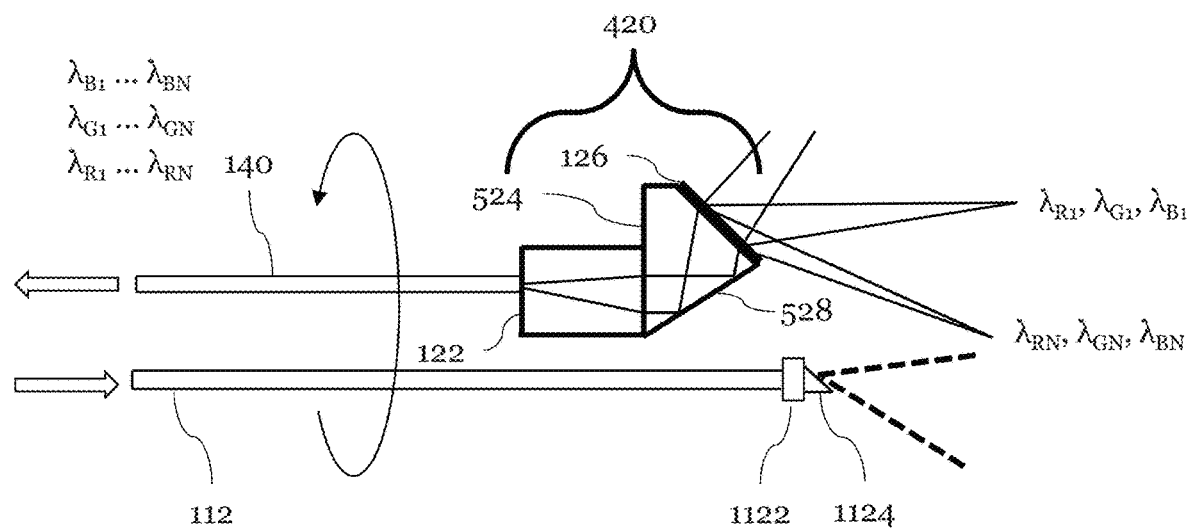
FIG. 11 shows schematic of a portion of another embodiment.

FIG. 11 is an illustration of a portion of an exemplary embodiment that includes a forward viewing SEE probe 420. In this embodiment, illumination fiber 112 and detection fiber 140 are exchanged when compared to the embodiment illustrated in FIG. 5. In which case the illumination light is not diffracted but the diffraction grating is used ensure only light with a certain is transmitted onto the detection fiber 140. This alternative embodiment may also include a cylindrical lens 1122 which is attached to the illumination waveguide 112. This alternative embodiment may also include a prism 1124 which is attached to the cylindrical lens 1122 so that illumination light on the sample 200 is a white line as opposed to 3 spectrally encoded lines as in the previous embodiment. Reflected light from the sample 200 is collected and passed along to the detection fiber 140 through grating 126 on the spacer 524, reflected by the surface 528 and focused by a lens 122. The illumination fiber 112 and the detection fiber 140 may rotate together. The white line may be aligned along a radial direction of the probe field of view, and rotates with the probe. The white line may be asymmetric with respect to the center of field of view due to distortion of the prism 134, so that light diffracted in only one order is coupled into the detection fiber 140.

In some embodiments, the probe, which may be either a forward view or side view probe, is a disposable probe. In these embodiments, the illumination fiber 112 and detection fiber 140 may be detachable. With this exemplary function, the probe may be disposable in order to ensure that a sanitary probe is being inserted into the subject which may be a human body.

According to various exemplary embodiments, multi-cladding fiber may be utilized. Multi-cladding fiber may act as if it has different core diameters depending on the light propagating direction. Thus, such multi-cladding fiber may be used as both the illumination fiber and the detection fiber. If the multi-cladding fiber is connected to a rotary junction, continuous rotation of the probe may be performed.

System and Software Related disclosure

Embodiment(s) of the present invention may also be realized by one or more computers that reads out and executes computer executable instructions (e.g., one or more programs) recorded on a transitory or non-transitory storage medium to perform the functions of one or more of the above-described embodiment(s) and/or that includes one or more circuits for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer system, for example, is part of or attached to the image processor and may obtain and modify information received from the imaging detector and an optional second detector.

In one embodiment, the image processor 150 includes one or more computer unit(s) and one or more display unit(s)

which may be connected to the image processor 150 via a high definition multimedia interface (HDMI). Optionally, a separate image server is another computer unit connected to the processor 150 connected via an Ethernet cable or the wireless access point.

Figure 12:
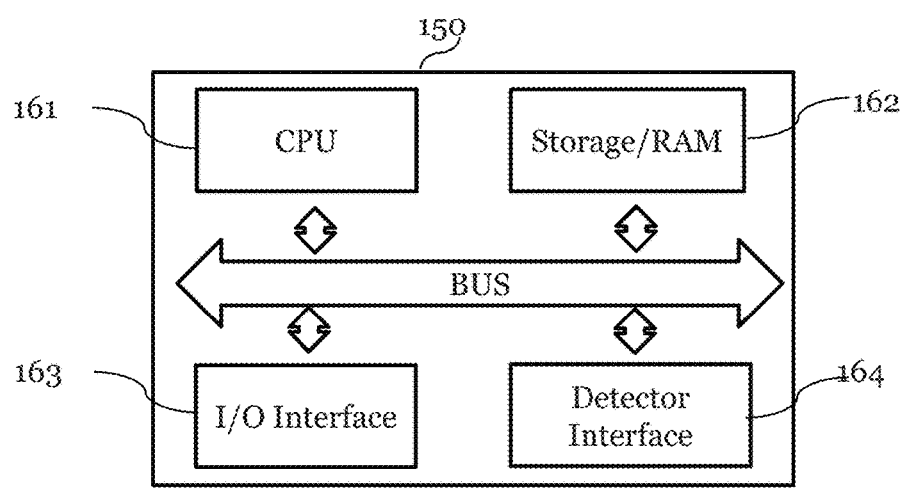
FIG. 12 shows a schematic of an exemplary imaging console as may be used in an embodiment.

FIG. 12 is an illustration of the image processor 150 where commands may be transmitted to one or more processor(s) 161 via a user interface unit/arrangement that may be located on the image processor 150. The image processor may include an I/O interface in which command are received via one or more an included or separately attached touch panel screen, keyboard, mouse, joy-stick, ball controller, and/or foot pedal. A user/operator may cause a command to be initiated so as to observe or gather information about a subject which may be inside a human body through an exemplary front-view SEE probe using the image processor 150. For example, when the user inputs a command, the command is transmitted to a CPU 161 for execution thereby.

The image processor 150 may include a CPU 161, Storage/RAM 162, I/O Interface 163 and a Detector Interface 164. Also, the image processor 150 may also comprise one or more devices. The image processor may include one or more general purpose computers or may include application specific processors, such as an ASIC, DSP, FPGA, GPU, FPU, etc.

The image processor 150 may be programmed to apply exemplary image processing such as noise reduction, coordinate distortion correction, contrast enhancement and so on. After or even during the image processing is performed, the data may be transmitted from the image processor 150 to a display. In some exemplary embodiments, a liquid crystal display may be the display. The display may display, for example, the individual images obtained from a single mode or a composite color image according to various exemplary embodiments of the present disclosure. The display may also display other information than the image, such as the date of observation, what part of the human body is observed, the patient's name, operator's name and so on.

The CPU 161 is configured to read and perform computer-executable instructions stored in the Storage/RAM 162. The computer-executable instructions may include those for the performance of the methods and/or calculations described herein. The Storage/RAM 162 includes one or more non-transitory computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 162 may store computer-readable data and/or computer-executable instructions. The components of the image processor 150 may communicate via a bus.

The I/O interface 163 provides communication interfaces to input and output devices, which may include a keyboard, a display, a mouse, a printing device, a touch screen, a light pen, an optical storage device, a scanner, a microphone, a camera, a drive, communication cable and a network (either wired or wireless).

The detector interface 163 also provides communication interfaces to input and output devices. The detector may include a detection system such as the spectrometer 142, components within the spectrometer, for example a photo-multiplier tube (PMT), a photodiode, an avalanche photo-diode detector (APD), a charge-coupled device (CCD), multi-pixel photon counters (MPPC), or other and also components that provide information about the state of the probe such as a rotary encoder, motor drive voltage, thermocouple, etc. Also, the function of detector may be realized by computer executable instructions (e.g., one or more programs) recorded on a Storage/RAM 162.

In an exemplary operation, the user may place the exemplary SEE probe into a sheath, and then may insert such arrangement/configuration into a predetermined position of a human body. The sheath alone may be inserted into the human body in advance, and it is possible to insert the SEE probe into the sheath after sheath insertion. The exemplary probe may be used to observe inside a human body and works as endoscope such as arthroscopy, bronchoscope, sinuscope, vascular endoscope and so on.

Definitions

In referring to the description, specific details are set forth in order to provide a thorough understanding of the examples disclosed. In other instances, well-known methods, procedures, components, and circuits have not been described in detail as not to unnecessarily lengthen the present disclosure.

It should be understood that if an element or part is referred herein as being "on", "against", "connected to", or "coupled to" another element or part, then it may be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90° or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

The foregoing merely illustrates the principles of the disclosure. Various modifications and alterations to the described exemplary embodiments will be apparent to those skilled in the art in view of the teachings herein. Indeed, the arrangements, systems and methods according to the exemplary embodiments of the present disclosure can be used with any SEE system or other imaging systems, and for example with those described in U.S. Pat. Nos. 6,341,036; 7,796,270; 7,843,572; 7,859,679; 8,045,177; 8,145,018; 8,780,176; 8,812,087; 9,295,391; and 9,254,089 and PCT publications WO2015/116951 and WO2015/116939, the disclosures of which are incorporated by reference herein in their entireties.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A system comprising a spectrally encoded endoscopy probe for color imaging comprising:
    a light guiding component for guiding illumination light;
    a light focusing component;
    a grating component, wherein the spectrally encoded endoscopy probe and/or the light guiding component, the light focusing component and grating component is/are configured such that a set of light beams of multiple wavelengths are diffracted in multiple or different orders at a same angle;
    wherein the set of light beams includes at least 3 light beams, and
    wherein each light beam among the set of light beams is associated with a different wavelength;
    a second light guiding component for guiding collected light;
    at least one detector; and
    a processor, wherein the processor is adapted and configured to form a color image based on information from the light diffracted in the multiple or different orders,
    wherein the second light guiding component includes multiple detection fibers that operate to pass the collected light to the at least one detector, and
    wherein the multiple detection fibers surround, are positioned around or along a perimeter of, and/or are spaced away from the light guiding component for guiding the illumination light.

2. The system of claim 1, wherein a ratio A over B of a diffraction order A among the different orders and a diffraction order B among the different orders is smaller than 2;
    wherein the grating component diffracts light of a first wavelength associated with the diffraction order A at a same angle as the grating component diffracts light of a second wavelength associated with the diffraction order B, or wherein light of the first wavelength associated with the diffraction order A is diffracted at the same angle as light of the second wavelength associated with the diffraction order B; and
    wherein the first wavelength is less than the second wavelength.

3. The system of claim 1, wherein the multiple detection fibers comprise 2, 3, 4, 5, 6, 7, 8, or greater than 8 detection fibers.

4. The system of claim 1, wherein one or more of the multiple detection fibers are stationary or rotate along with the light guiding component for guiding the illumination light.

5. The system of claim 1, wherein the multiple detection fibers form a fiber bundle having a distal end and a proximal end, wherein the distal end of the fiber bundle has a fiber array shape that is different than a fiber array shape of the proximal end of the fiber bundle.

6. The system of claim 1, wherein the spectrally encoded endoscopy probe and/or the system further includes a time gate operating to select which detection fiber or detection fibers of the multiple detection fibers is or are used.

7. The system of claim 1, wherein the at least one detector comprises a spectrometer.

8. The system of claim 7, wherein the spectrometer includes a line sensor having tall pixels or a sensor array having tall pixels, each of the tall pixels being made of a plurality of smaller pixels.

9. The system of claim 8, wherein one or more of the following:
    (i) each pixel in the line sensor or the sensor array is a rectangular pixel;
    (ii) each pixel in the line sensor or the sensor array is a rectangular pixel 24 μm×500 μm; and
    (iii) the line sensor or the sensor array operates to produce an image in which spectral information is along a first axis and spatial information from the second light guiding component is along a second axis orthogonal to the first axis.

10. The system of claim 1, wherein one or more of the following:
    (i) the spectrally encoded endoscopy probe and/or the system further includes a beam block; and
    (ii) the beam block is positioned around the grating component such that the beam block operates to block light which is diffracted at angles other than those angles in a predetermined field of view.

11. The system of claim 10, wherein the beam block operates to block other orders having a diffraction angle that is smaller than the diffracted light which illuminates a sample or that is smaller than light diffracted from the grating component.

12. The system of claim 10, wherein the beam block is tubing.

13. The system of claim 10, wherein the beam block is stationary or operates to rotate along with the light guiding component for guiding the illumination light.

14. The system of claim 1, wherein the multiple or different orders of spectrally dispersed light are −m, −(m+1)$^{th}$, and −(m+2)$^{th}$ diffraction orders, and wherein m is an integer.

15. The system of claim 14, further comprising a beam block positioned outside the probe field of view to block light beams diffracted in orders which are not the multiple or different orders.

16. The system of claim 1, wherein the second light guiding component comprises one or more angle polished optical fibers.

17. The system of claim 1, further comprising:
a scanner for scanning the set of light beams in a first direction;
wherein the processor is further configured to apply a smoothing function with a kernel in the first direction to the information from the light diffracted in the multiple or different orders;
wherein the kernel is a first size for a first subset of wavelengths for each of the multiple or different orders;
wherein the kernel is a second size for a second subset of wavelengths for each of the multiple or different orders; and
wherein the first size is different from the first size.

18. The system of claim 17, wherein
the color image is a polar image;
the first subset of wavelengths for each of the multiple or different orders is associated with a first range of radii of the polar image;
the second subset of wavelengths for each of the multiple or different orders is associated with a second range of radii of the polar image;
the first range of radii is less than the second range of radii; and
the first size of the kernel is larger than the second size of the kernel.

19. A system comprising a spectrally encoded endoscopy probe for color imaging comprising:
a light guiding component for guiding illumination light;
a light collecting component that comprises a first grating, and a lens; and
a second light guiding component for guiding collected light;
at least one detector; and
a processor, wherein the processor is adapted and configured to form a color image based on information from the collected light,
wherein the spectrally encoded endoscopy probe is configured such that a set of collected light beams of multiple wavelengths are diffracted in multiple or different orders and coupled into the second light guiding component by the light collecting component,
wherein the set of collected light beams includes at least 3 light beams,
wherein each light beam among the set of collected light beams is associated with a different wavelength,
wherein the spectrally encoded endoscopy probe is configured such that each of the collected light beams among the set of collected light beams that is coupled into the second light guiding component is diffracted by the first grating in a substantially single diffraction order, and
wherein the second light guiding component includes multiple detection fibers that operate to pass the collected light to the at least one detector, and the multiple detection fibers surround, are positioned around or along a perimeter of, and/or are spaced away from the light guiding component for guiding the illumination light.

20. A system comprising a spectrally encoded endoscopy probe for color imaging comprising:
a light guiding component for guiding illumination light;
a light focusing component;
a grating component, wherein the spectrally encoded endoscopy probe and/or the light guiding component, the light focusing component and grating component is/are configured such that a set of light beams of multiple wavelengths are diffracted in multiple or different orders at a same angle;
wherein the set of light beams includes at least 3 light beams, and
wherein each light beam among the set of light beams is associated with a different wavelength;
a second light guiding component for guiding collected light;
at least one detector; and
a processor, wherein the processor is adapted and configured to form a color image based on information from the light diffracted in the multiple or different orders,
wherein the second light guiding component includes multiple detection fibers that operate to pass the collected light to the at least one detector, and
wherein the multiple detection fibers form a fiber bundle having a distal end and a proximal end, wherein the distal end of the fiber bundle has a fiber array shape that is different than a fiber array shape of the proximal end of the fiber bundle.

21. A system comprising a spectrally encoded endoscopy probe for color imaging comprising:
a light guiding component for guiding illumination light;
a light focusing component;
a grating component, wherein the spectrally encoded endoscopy probe and/or the light guiding component, the light focusing component and grating component is/are configured such that a set of light beams of multiple wavelengths are diffracted in multiple or different orders at a same angle;
wherein the set of light beams includes at least 3 light beams, and
wherein each light beam among the set of light beams is associated with a different wavelength;
a second light guiding component for guiding collected light;
at least one detector; and
a processor, wherein the processor is adapted and configured to form a color image based on information from the light diffracted in the multiple or different orders,
wherein the spectrally encoded endoscopy probe and/or the system further includes a beam block, and
wherein the beam block is tubing.

22. The system of claim 21, wherein one or more of the following:
(i) the beam block is positioned around the grating component such that the beam block operates to block light which is diffracted at angles other than those angles in a predetermined field of view;
(ii) the beam block operates to block other orders having a diffraction angle that is smaller than the diffracted light which illuminates a sample or that is smaller than light diffracted from the grating component; and/or
(iii) the beam block is stationary or operates to rotate along with the light guiding component for guiding the illumination light.

* * * * *

UNITED STATES PATENT AND TRADEMARK OFFICE
CERTIFICATE OF CORRECTION

PATENT NO. : 10,732,400 B2
APPLICATION NO. : 16/509292
DATED : August 4, 2020
INVENTOR(S) : Mitsuhiro Ikuta et al.

It is certified that error appears in the above-identified patent and that said Letters Patent is hereby corrected as shown below:

In the Claims

Column 19, Line 20, Claim 17 should be changed from "wherein the first size is different from the first size." to --wherein the first size is different from the second size.--

Signed and Sealed this
Twenty-second Day of September, 2020

Andrei Iancu
*Director of the United States Patent and Trademark Office*